United States Patent [19]

Martel et al.

[11] 4,206,140
[45] Jun. 3, 1980

[54] NOVEL CYCLOPROPANECARBOXYLIC ACIDS AND ESTERS

[75] Inventors: Jacques Martel, Bondy; Chanh Huynh, Villemomble; Jean Buendia, Fontenay-sour-Bois, all of France

[73] Assignee: Roussel Uclaf, Paris, France

[21] Appl. No.: 910,695

[22] Filed: May 30, 1978

Related U.S. Application Data

[60] Division of Ser. No. 749,402, Dec. 10, 1976, Pat. No. 4,101,570, which is a division of Ser. No. 395,146, Sep. 7, 1973, Pat. No. 3,997,586, which is a division of Ser. No. 168,441, Aug. 2, 1971, Pat. No. 3,786,052, which is a continuation-in-part of Ser. No. 879,942, Nov. 25, 1969, abandoned, and Ser. No. 662,278, Aug. 22, 1967, abandoned.

[30] Foreign Application Priority Data

| Aug. 26, 1966 [FR] | France | 66.74404 |
| Aug. 26, 1966 [FR] | France | 66.74405 |
| Feb. 24, 1967 [FR] | France | 67.96425 |
| Jun. 16, 1967 [FR] | France | 67.110719 |
| Jul. 19, 1967 [FR] | France | 67.114833 |
| Nov. 26, 1968 [FR] | France | 68.175375 |

[51] Int. Cl.² .................... C07C 61/18; C07C 61/28
[52] U.S. Cl. .................... 260/544 L; 260/544 P
[58] Field of Search .................... 260/544 L, 544 P

[56] References Cited

U.S. PATENT DOCUMENTS

| 3,766,218 | 10/1973 | Ueda et al. | 260/544 L |
| 3,989,750 | 11/1976 | Tsuneyuki et al. | 260/544 L |
| 4,024,163 | 5/1977 | Elliott et al. | 260/544 L |

*Primary Examiner*—Norman Morgenstern
*Attorney, Agent, or Firm*—Hammond & Littell, Weissenberger and Muserlian

[57] ABSTRACT

Novel cyclopropanecarboxylic acids and esters of the formula

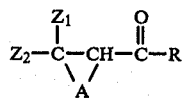

wherein $Z_1$ and $Z_2$ are selected from the group consisting of hydrogen, alkyl, aralkyl, aryl, alkenyl non-conjugated with the cyclopropane ring, alkynyl non-conjugated with the cyclopropane ring, cycloalkyl, cycloalkenyl and heterocyclic; R is selected from the group consisting of OH and OR' in which R' is selected from the group consisting of lower alkyl which may be substituted, benzyl which may be substituted on the phenyl or methylene portion, N-methylene-dicarboximide, (5-benzyl-furyl-3) methyl, and a cyclopentene of the formula

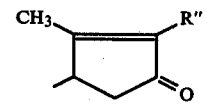

wherein R" is selected from the group consisting of alkyl, alkynyl, alkenyl, aryl, aralkyl, cycloalkyl, cycloalkenyl and heterocyclic; A is a bivalent alkyl radical selected from the group consisting of

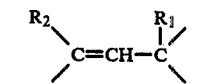

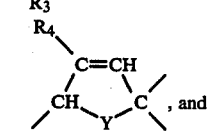

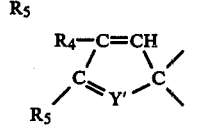

wherein $R_1$ is selected from the group consisting of hydrogen and lower alkyl, $R_2$ and $R_3$ are selected from the group consisting of alkyl, alkynyl, alkenyl, aryl, aralkyl, cycloalkyl, cycloalkenyl and heterocyclic and taken together with the carbon atom to which they are attached form a ring selected from the group consisting of carbon homo rings and unsaturated carbon homo rings of 3 to 7 carbon atoms and heterocyclic rings which may be substitued with lower alkyl or lower alkoxy and $R_2$ and $R_3$ may together form a polycyclic aromatic radical, $R_4$ is lower alkyl, $R_5$ is selected from the group consisting of hydrogen and lower alkyl and $R_4$ and $R_5$ together with the carbon atoms to which they are attached may form a saturated or unsaturated carbon homo ring or a heterocyclic ring, Y is selected from the group consisting of methylene and a saturated or unsaturated carbon chain and Y' is selected from the group consisting of methine and a saturated or unsaturated carbon chain with the proviso that when $Z_1$ and $Z_2$ are methyl and $R_1$ is hydrogen, $R_2$ is other than methyl and their preparation.

3 Claims, No Drawings

NOVEL CYCLOPROPANECARBOXYLIC ACIDS AND ESTERS

PRIOR APPLICATION

This application is a divisional application of application Ser. No. 749,402 filed Dec. 10, 1976, now Pat. No. 4,101,570 which is a division of U.S. Patent Application Ser. No. 395,146 filed Sept. 7, 1973, now U.S. Pat. No. 3,997,586 which in turn is a division of copending application Ser. No. 168,441 filed Aug. 2, 1971, now U.S. Pat. No. 3,786,052 which in turn is a continuation-in-part application of our copending, commonly-assigned U.S. patent applications Ser. No. 662,278 filed Aug. 22, 1967 and No. 879,942 filed Nov. 25, 1969 now both abandoned.

OBJECTS OF THE INVENTION

It is an object of the invention to provide the novel cyclopropanecarboxylic acids and esters of Formula I.

It is another object of the invention to provide a novel process for the preparation of the compounds of Formula I.

It is an additional object of the invention to provide novel insecticidal compositions having low toxicity to warm blooded animals.

These and other objects and advantages of the invention will become obvious from the following detailed description.

THE INVENTION

The novel cyclopropanecarboxylic acids and esters of the invention have the structure of Formula I and are important compounds. The free acids (where $R = CH$) can be esterified with or converted into a functional derivative thereof which can be esterified with an alcohol of the formula $HOR'$ to obtain the corresponding esters which have insecticidal properties and an anthelmintic activity.

The preferred compounds of the invention are a racemic or optically-active cyclopropanecarboxylic derivative having the formula:

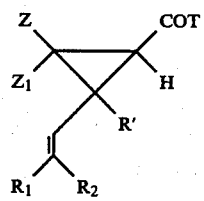

wherein Z and $Z_1$ are selected from the group consisting of lower alkyl having from 1 to 7 carbon atoms and phenyl and Z and $Z_1$ together represent an alkylene residue having 4 to 5 carbon atoms, T is selected from the group consisting of hydroxyl, chlorine and $OT'$, $T'$ being selected from the group consisting of alkali-metal anions, anions of optically active organic bases, lower alkyl, (5-benzylfuryl-3)-methyl, and 2-T''-3-methyl-1-oxo-2-cyclopentene-4-yl (T'' is selected from the group consisting of lower alkenyl, cycloalkenyl of 3 to 7 carbon atoms, and furfuryl) $R_1$ and $R_2$ are selected from the group consisting of lower alkyl and phenyl and may together represent an alkylene residue having 3 to 7 carbon atoms which may be interrupted by an heteroatom and which may be substituted by at least one substituent selected from the group consisting of lower alkyl and lower alkoxy $R'$ is selected from the group consisting of hydrogen and lower alkyl or form together with $R_2$ an alkylene residue which may be unsaturated or substituted by a carbon chain with the proviso that when Z and $Z_1$ are methyl and $R'$ is hydrogen, $R_2$ is other than methyl. Most preferred are compounds where $R'$ is hydrogen in trans configuration in relation to the carboxylic chain and $R_1$ and $R_2$ together form a butylidene chain.

The esters of Formula I in which $R'$ is 2-R''-3-methyl-1-oxo-2-cyclopentene-4yl wherein $R''$ has the above definition are particularly distinguished by a strong insecticidal activity and a low toxicity to humans and warm blooded animals. Examples of said esters are those wherein $R''$ is allyl, cis-2-butenyl, cis-2,4-pentadienyl, 2-cyclopentenyl, cyclohexyl, 2-cyclohexenyl, 2-propynyl and 2-furyl-methyl.

The following esters of Formula I have been found to possess a marked insecticidal activity: the d,l-allethrolone esters of d,l-trans 3,3-dimethyl-2-(2'-ethyl-1'-butenyl)-cyclopropanecarboxylic acid, d, 1-trans 3,3-dimethyl-2-cyclopentylidenemethyl-cyclopropanecarboxylic acid, d, 1-trans 3,3-dimethyl-2-cyclohexylidenemethyl-cyclopropanecarboxylic acid, d, 1-trans 3,3-dimethyl-2-cyclopropylidene-methyl-1-cyclopropanecarboxylic acid and d, 1-trans 3,3-dimethyl-2-cyclobutylidenemethyl-1-cyclopropanecarboxylic acid; the cis-cinerolone esters of d, 1-trans 3,3-dimethyl-2-cyclopentylidenemethyl-1-cyclopropanecarboxylic acid; the 1-oxo-3-methyl-2-82'-cyclohexenyl)-2-cyclopentene-4-ol ester of d, 1-trans 3,3-dimethyl-2-cyclopentylidenemethyl-cyclopropanecarboxylic acid; and the (5-benzyl-furyl-3)-methyl alcohol ester of d, 1- and d-trans 3,3-dimethyl-2-cyclopentylidene-methyl-1-cycloprpanecarboxylic acid. The said esters have been found to be effective against such insects as house flies, grain weevils, american cockroaches, german cockroaches, yellow fever mosquitos at dosages depending on the way they are used. More particularly they may be associated with synergists such as piperonyl butoxide and spread by means of aerosols, spacesprays or powders.

The novel process of the invention comprises reacting an alkali metal aryl sulfinate of the formula $$ArSO_2M \qquad \qquad II$$

wherein M is an alkali metal such as sodium or potassium and Ar is an aryl radical of 1 to 2 aromatic rings which may be substituted with at least one substituent selected from the group consisting of lower alkyl, lower alkoxy, halogen, nitro and halo methyl with an allylic halogen derivative of the formula $$H\text{—}A\text{—}X \qquad \qquad III$$

wherein A has the above definition and X is selected from the group consisting of chlorine, iodine, bromine, mesyl and tosyl to form the corresponding aryl allyl sulfone of the formula

wherein A and Ar have the above definitions, reacting the latter in the presence of a basic agent with an $\alpha,\beta$-ethylenic ester of the formula

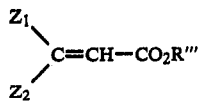

wherein $Z_1$ and $Z_2$ have the above definition and $R'''$ is a substituted or unsubstituted lower alkyl radical to form an ester of the formula

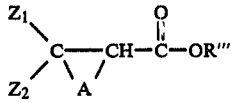

wherein A, $R'''$, $Z_1$ and $Z_2$ have the foregoing definition, hydrolyzing the latter under alkaline conditions to form the corresponding free acid, preferably converting the latter into a functional derivative such as acid halide, anhydride, mixed anhydride, ester or metal salt, reacting the functional derivative or the free acid with an alcohol of the formula

NR' wherein R' has the foregoing definition and N is selected from the group consisting of hydroxy and halide to form the corresponding ester of Formula I.

A preferred embodiment of the process for the preparation of a compound of the formula:

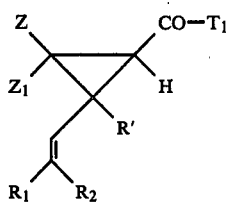

wherein Z and $Z_1$ are defined as above, $T_1$ is selected from the group consisting of Cl, OH and OT', T' is selected from the group consisting of alkali-metal anions, anions of an organic optically-active base, lower alkyl, (5-benzyl furyl-3) methyl, and 2-T''-3-methyl-1-oxo-2-cyclopenten-4-yl, T'' being selected from the group consisting of lower alkenyl, cycloalkenyl having from 3 to 7 carbon atoms and furfuryl.

R', and $R_1$ and $R_2$ are defined as above comprises reacting an alkali-metal salt of an aryl-sulfinate of the formula:

Ar SO$_2$ M wherein M is an alkali-metal and Ar is an aryl radical having 1 to 2 aromatic rings which may be substituted with at least one substituent selected from the group consisting of lower alkyl, lower alkoxy, halogen, nitro and halomethyl, with an allylic halide having the formula:

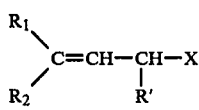

wherein R' is selected from the group consisting of hydrogen and lower alkyl or form together with $R_2$ an alkylene residue which may be unsaturated or substituted by a carbon chain, X is selected from the group consisting of chlorine, bromine, iodine, methyl sulfonyloxy, p-toluenesulfonyloxy and hydroxy with the proviso that when X is OH, the reaction is performed in the presence of formic acid—and $R_1$ and $R_2$ have the above defined meanings, to form the corresponding arylalkylsulfone of the formula:

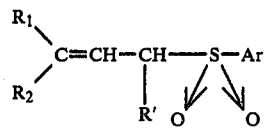

wherein the substituents R', Rhd 1, $R_2$ and Ar have the same meanings as above and reacting the said sulfone with the ester of a α,β-unsaturated aliphatic carboxylic acid of the formula:

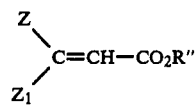

wherein Z and $Z_1$ are defined as above and $R''$ is a lower alkyl to form the corresponding ester of a cyclopropyl carboxylic acid of the formula:

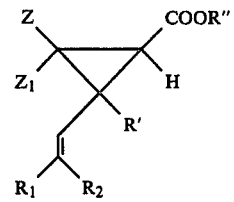

wherein Z, $Z_1$, R', $R_1$, $R_2$ and $R''$ are defined as above, saponifying the latter under alkaline conditions if desired to form the corresponding racemic cyclopropane carboxylic acid, resolving the latter if desired with an optically active organic base, converting the said racemic or optically- active acid into a functional derivative selected from the group consisting of acid chloride, acid bromide, anhydride, mixed anhydride, esters and salts thereof, and reacting the said functional derivative with a compound of the formula T-X' wherein X' is hydroxy or halogen and T has the above-definition, and recovering the desired ester.

The process of the invention has the advantage of simplicity since it synthesizes a substituted cyclopropane in a single step from readily available raw materials or from materials which can be prepared without any greater difficulty and the process can be operated without any hazards. Known methods of producing cyclopropanecarboxylic acids or their esters require the preparation and use of relatively unstable diazo compounds such as diazeoacetonitrile or diazoacetic acid esters or to avoid this hazard required a multiple step process having rather poor yields in some steps.

Another advantage of the process of the invention is the general nature thereof whereby a large variety of differently substituted compounds may be made. In the aryl allyl sulfones of Formula IV, for example, the aryl group may be homo or polycyclic and may be substituted with numerous different substituents, the p-tolyl group furnishing particularly excellent results. More important, the allyl group of the aryl allyl sulfone can have most varied structures and may be of the linear type such as

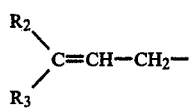

wherein $R_2$ and $R_3$ may be, for example, ethyl, isopropyl, phenyl, cycloalkyl or together may form a 5 carbon ring or a heterocyclic or the cyclic type such as

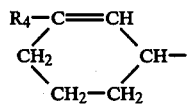

wherein $R_4$ may be alkyl.

The process of the invention is so general that the aryl allyl sulfone of Formula IV may not only be reacted with an ester of Formula V but also with other $\alpha,\beta$-ethylenic carbonyl compounds such as ketones, nitriles and conjugated amides to form the corresponding cyclopropanecarboxylic acid ester.

The preparation of the aryl allyl sulfones of Formula IV is preferably effected in a solvent such as a methanol or ethanol medium in the presence of a basic agent such as alkali metal carbonates or acetates. Preferably, the said reaction is effected in methanol in the presence of sodium or potassium carbonate.

As a modification of the process, the aryl allyl sulfones can be prepared by reacting an alkali metal aryl sulfinate with an alcohol of the formula

wherein A has the above definition in the presence of formic acid or by the method described in French Pat. No. 1,483,715.

The alkali metal aryl sulfinates of Formula II can be prepared by known processes such as reduction of aryl sulfonyl chlorides to aryl sulfinic acids which are converted into the corresponding alkali metal salts. The acrylic acid esters of Formula V are prepared also by known methods and are preferably the lower alkyl esters such as methyl, ethyl or n-butyl.

The reaction of the aryl allyl sulfone and the acrylic ester of Formula V is effected in an anhydrous organic medium in the presence of a basic agent, preferably an alkali metal amide, hydride or alcoholate or dimsyl sodium. Particularly advantageous basic agents are sodium methylate, sodium tert.-amylate and potassium tert.-butylate. The organic solvent may be selected from the group consisting of aromatic hydrocarbons such as benzene, toluene, etc.; ethers such as tetrahydrofuran; and preferably aprotic dipolar solvents such as dimethylformamide, dimethylsulfoxide, hexamethylene-phosphoramide or acetonitrile. In the most preferred process the reaction is performed in tetrahydrofuran in the presence of potassium tert.-butylate or in benzene in the presence of sodium tert.-amylate or in dimethylformamide in the presence of potassium tert.-butylate or in dimethylsulfoxide in the presence of sodium methylate or in dimethylsulfoxide in the presence of potassium tert.-butylate.

An additional advantage of the process of the invention occurs when A has the structure

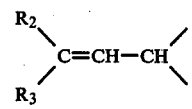

and $R_2$ and $R_3$ are other than aryl since the corresponding esters of Formula 1 in which $R=OR'''$ are selectively in the trans form and unexpectedly no trace of the cis-isomer is found. By saponification and re-esterification, it is possible to isolate first the trans acid ($R=OH$) and the esters ($R=OR'$) of the trans acid. These synthesized compounds therefore possess the same stereochemistry as natural chrysanthemic acid and its esters. When $R_2$ and $R_3$ are aryl, the selectivity is not so strict.

When A has the structure

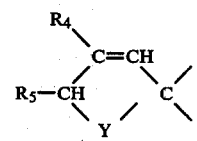

the compound of Formula I being of the spiro type, the two theoretically possible isomers can be isolated and these isomers have been designated as the cis isomer and the trans isomer. They may be represented as follows:

Trans isomer         Cis isomer

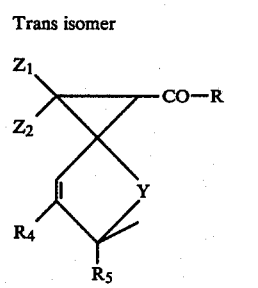 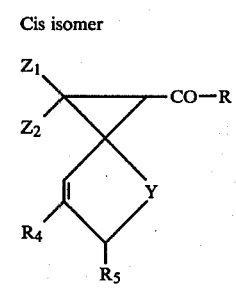

Although it is not necessary to postulate the mechanism for the formation of the cyclopropanecarboxylic acid esters in which R is $OR'''$ from the aryl allyl sulfone and the $\alpha,\beta$-ethylenic ester, the reaction can be considered to take place in two steps. In the first step, the sulfone function of the compound of Formula IV activates the methylene and methine group in the $\alpha$-position thereby inducing the 1,4-addition of the sulfone to the conjugated double bond of the said ester, notwithstanding the unfavorable steric and electron effects of $Z_1$ and $Z_2$. After protonation of the intermediate adduct, the formation of a compound of Formula VII was ascertained

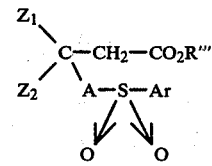

which may actually exist in the basic and aprotic reaction medium in the form of an $\alpha$-carboalkoxylic anion or its enol form. In the second step which may occur simultaneously, the sulfone function of the intermediate of Formula VII or its carboalkoxylic or enol anion plays a new role due to its ability to be eliminated in the form of an ArSO₂-sulfinic anion thereby promoting the intramolecular cyclization to form the cyclopropanecarboxylic acid ester in which R is OR‴. However, the invention is not intended to be limited to the above theoretical considerations. Moreover, the invention covers the entire process where an intermediate of Formula VII or an analog is isolated and then reacted to form the said cyclopropanecarboxylic acid ester.

The hydrolysis of the cyclopropanecarboxylic acid esters wherein R is-OR‴ to the free acids may be effected with an alkali metal hydroxide such as sodium hydroxide or potassium hydroxide and is usually effected in an aqueous alcohol medium such as methanol, ethanol or glycol.

The conversion of the free cyclopropanecarboxylic acids of Formula I into the esters where R is —OR' can be obtained by various methods with reaction of the corresponding alcohol. The alcohol may be directly reacted with the said acid in the presence of a strong acid catalyst, preferably with azeotrophic distillation of the water of reaction formed.

However, it may be advantageous to first convert the said free acid into an acid function derivative such as its acid anhydride, a mixed acid anhydride, its acid chloride or a metal salt which can then be reacted with the appropriate alcohol to obtain the desired ester of Formula I. The acid anhydride can be obtained by reaction of acetic acid anhydride and the said free acid, for example.

The cyclopropanecarboxylic acid chloride can be formed by reacting the free acid of Formula I with a chlorinating agent such as thionyl chloride, phosphorus trichloride, phosphorus pentachloride, etc. Preferably, the said acid is reacted with thionyl chloride in a benzene medium to form the acid chloride which is then reacted with the appropriate alcohol in an aromatic hydrocarbon solvent such as benzene or toluene in the presence of a tertiary amine such as pyridine to bind the hydrochloric acid formed.

A metal salt of the cyclopropanecarboxylic acid of Formula I can be formed by neutralizing the said acid with an alcohol solution of alkali metal alcoholate followed by removal of the solvent and the alkali metal salt of the said acid can then be reacted with a halogenated derivative, preferably the bromine derivative, of the alcohol in dimethylformamide to form the desired ester.

As a modification of the said process, the cyclopropanecarboxylic acid esters where R is OR‴ may be transesterified with the desired alcohol by heating the reactants in the presence of sodium while continuously distilling off the freed lower alcohol. However, it is sometimes advantageous for purification to saponify the said acid ester to form the free acid, react the latter to form again a lower alkyl ester such as with diazomethane to form the methyl ester and subjecting the latter ester to trans-esterification with the desired alcohol.

In another modification of the process of the invention wherein $R_2$ and $R_3$ are alkyl of 1 to 6 carbon atoms or taken together with the carbon atom to which they are attached form a cycloalkyl of 3 to 6 carbon atoms, racemic trans-3,3-dimethyl-2-formyl-cyclopropane-1-carboxylic acid or of (1R,2R) or (1S,2S) configuration, or an alkyl ester of these compounds of formula A:

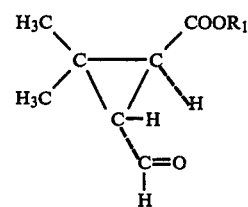

in which $R_1$ is hydrogen or alkyl of 1 to 4 carbon atoms is reacted in the presence of a strong base with a phosphonium salt of formula B:

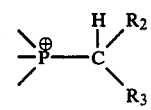

in which $R_2$ and $R_3$ have the afore-mentioned meaning. This phosphonium salt is able to exist in the basic medium in the form of an ylide, of formula B':

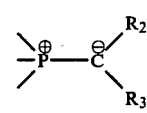

in order to obtain racemic trans-3,3-dimethyl-2-R'-cyclopropane-1-carboxylic acid or of (1R,2R) or (1S,2S) configuration, or an alkyl ester of these compounds of formula Ia of the same configuration at 1 and at 2 as the starting compound

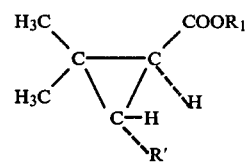

wherein $R_1$ and R' have the afore-mentioned meaning, and hydrolyzing the condensation product with an alkaline agent when $R_1$ is an alkyl of 1 to 4 carbon atoms to isolate the corresponding racemic 3,3-dimethyl-2-R'-cyclopropane-1-carboxylic acid or of (1R,2R) or (1S,2S) configuration, of formula Ib

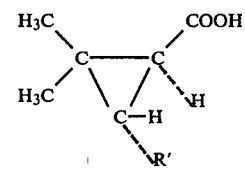

wherein R' has the afore-mentioned meaning.

Among the phosphonium salts of formula B, which are condensed with the acid or ester of formula A are salts of triaryl phosphonium, specifically salts of triphenylphosphonium, salts of tris (dialkylamino) phosphonium, of [(bis dialkylamino)-aryl] phosphonium and of (dialkylamino-diaryl) phosphonium which all give rise to an ylide of the formula B' under the action of strong bases. As the phosphonium salt, the iodide and bromide are preferred.

Among the strong bases, in the presence of which condensation of the phosphonium salt of formula B with the aldehyde of formula A is effected, one can mention specifically alkali metal hydrides, alkali metal amides, alkali metal alcoholates or alkyl lithiums.

Condensation of the aldehyde of formula A with the phosphonium salt of formula B is conveniently effected in an organic solvent such as diethylene glycol monomethyl ether, diethyleneglycol diethyl ether, ethyl ether, dimethyl sulfoxide, dimethyl-formamide, tetrahydrofuran, dimethoxyethane or benzene. Excellent results may be obtained by the use of an alkali metal alcoholate in the presence of dimethylsulfoxide or of an alkyl lithium in the presence of dimethoxyethane or benzene.

After condensation of the ylide of formula B' with the aldehyde of formula A, the crude reaction product is purified by conventional methods. For example, the product can be treated with reagent T of Girard to eliminate by solubilization in the aqueous phase the unreacted aldehyde fraction or purified by pasting or crytallization from a suitable solvent. When the starting aldehyde of formula A is an ester, the crude reaction product can be purified by rectification.

The cyclopropyl or cyclobutyl triaryl phosphonium halide is preferably cyclopropyl or cyclobutyl tri-phenyl phosphonium halide. The basic agent used to effect the condensation of the cyclopropyl or cyclobutyl triaryl phosphonium halide with dl-trans caronaldehyde acid is preferably an alkali metal hydride such as sodium or potassium hydride and the condensation is preferably conducted in a medium of dimethoxyethane or dimethoxypropane. Other bases such as alkali metal amides and other solvents such as tetrahydrofuran may be used.

The preparation of cyclopropyl triphenyl phosphonium bromide by thermal decomposition of 3-(2-oxotetrahydrofuranyl) triphenyl phosphonium bromide is described by H. Hartung (Angew. Chem. Int. Ed. 4, Page 704 (1965)). The preparation of cyclobutyl triphenyl phosphonium bromide by cyclization of 4-bromobutyl triphenyl phosphonium bromide is described by A. Mondon, Ann. 603, 115 (1957). Other cyclopropyl and cyclobutyl triaryl phosphonium halides can be prepared by similar processes. dl-trans caronaldehyde acid (or dl-trans 3-formyl-2,2-dimethyl-cyclopropanecarboxylic acid) can be prepared by the method described by M. Matsui et al [(Agr. Biol. Vol. 27, No. 8, pages 554–557 (1963)].

The 2-R''-3-methyl-1-oxo-2-cyclopentene-4-ol wherein R'' has the above definition, may be prepared by the process described in J.A.C.S., Vol. 71 (1949), p. 1 517 or modification of this process or by degradation of natural products.

Racemic mixtures of the cyclopropanecarboxylic acids of Formula I can be resolved with optically active organic bases such as ephedrine, if desired.

The cyclopentenolone esters of Formula I prepared by the process of the invention as a rule consist of a mixture of diastereoisomers. For example, the ester obtained by esterification of a d,l-trans cyclopropanecarboxylic acid of Formula I when R is OH with dl-allethrolone may consist of four diastereoisomers forming two racemates in varying proportions: one racemate consists of the ester of the $(\div)$-trans acid with $(\div)$-allethrolone and of the ester of the $(-)$-trans acid with $(-)$-allethrolone and the second racemate consists of the ester of the $(\div)$-trans acid ester with $(-)$-allethrolone and of the ester of $(-)$-trans acid with $(\div)$-allethrolone. As another example, the ester obtained by starting with a dl-trans cyclopropanecarboxylic acid of Formula I and $(\div)$-cinerolone consists of two diastereoisomers: the ester of the $(\div)$-trans acid with $(\div)$-cinerolone and the ester of the $(-)$-trans acid with $(+)$-cinerolone.

A preferred group of compounds of Formula I are those compounds wherein $Z_1$ and $Z_2$ are selected from the group consisting of hydrogen; lower alkyl of 1 to 7 carbon atoms such as methyl, ethyl, propyl, n-butyl; phenyl which may be substituted; phenyl lower alkyl; lower alkenyl nonconjugated with the cyclopropyl ring; lower alkynyl nonconjugated with the cyclopropyl ring; cycloalkyl and cycloalkenyl of 3 to 7 carbon atoms such as cyclopentyl, cyclohexyl, cyclohexenyl, etc.; and heterocyclic such as furyl; R' is selected from the group consisting of lower alkyl which may be substituted such as methyl, ethyl, halo ethyl, etc.; benzyl which may be substituted on the methylene with a lower alkyl or on the phenyl with halogen, lower alkyl, lower alkoxy, halo lower alkyl, lower alkenyl, etc.; N-methylene dicarboximides; 2-R''-3-methyl-1-oxo-2-cyclopentene-4-yl wherein R'' is selected from the group consisting of lower alkyl such as methyl; lower alkenyl such as allyl, butenyl, pentadienyl; alkynyl such as ethynyl; phenyl which may be substituted; phenyl lower alkyl; cycloalkyl and cycloalkenyl of 3 to 7 carbon atoms such as cyclohexyl, cyclopentenyl, cyclohexenyl; heterocyclic such as furfuryl; and (5-benzyl-furyl-3)-methyl; $R_2$ and $R_3$ are selected from the group consisting of lower alkyl, lower alkynyl, lower alkenyl, phenyl lower alkyl, phenyl which may be substituted, cycloalkyl and cycloalkenyl of 3 to 7 carbon atoms which may be substituted with lower alkyl and/or lower alkoxy and $R_2$ and $R_3$ together may form a polycyclic radical such as fluorene or together with the carbon atom to which they are attached may form a cycloalkyl, cycloalkenyl and heterocyclic of 3 to 7 carbon atoms such as cyclohexenyl, cyclopentadienyl which may be substituted with lower alkyl and/or lower alkoxy; $R_4$ is lower alkyl such as methyl; $R_5$ is hydrogen or lower alkyl and $R_4$ and $R_5$ together with the carbon atoms to which they are attached form a cycloalkyl, cycloalkenyl or heterocyclic of 3 to 7 carbon atoms; Y is methylene and Y' is methine.

In the following examples there are described several preferred embodiments to illustrate the invention. However, it should be understood that the invention is not intended to be limited to the specific embodiments.

PREPARATION OF REACTANTS

I. Preparation of 3-ethyl-1-pentene-3-ol

A solution of 93 gm of 3-pentanone in 100 cc of tetrahydrofuran were introduced over one hour into 615 cc of a solution of vinyl magnesium chloride in tetrahydrofuran titrating 1.78 moles/liter under an atmosphere of nitrogen and at a temperature not above 50° C. The mixture was agitated at room temperature for 15 hours. Thereafter, the reaction mixture was cooled to 0° C. and 500 cc of water were added under vigorous agitation and at a temperature not exceeding +40° C. The organic phase was separated by decanting and after the aqueous phase was extracted with ether the organic phases were combined and dried over magnesium sulfate. Then the solvents were eliminated and the residue obtained was rectified under atmospheric pressure, to obtain 95 gm of 3-ethyl-1-pentene-3-ol having a boiling point of 131° C.–132° C. and a refractive index $n_D^{21}=1.4345$, which was utilized as such for the preparation of 1-bromo-3-3thyl-2-pentene.

Working in the same fashion, but starting with 4-heptanone, 3-propyl-1-hexene-3-ol having a boiling point of 64°-68° C. under 14 mm Hg and a refractive index $n_D^{24}=1.438$ was obtained.

By starting with 2,4-dimethyl-pentane-3-one, 3-isopropyl-4-methyl-1-pentene-3-ol having a boiling point of 71°-75° C. under 30 mm pressure of mercury and a refractive index $n_D^{22}=1.443$ was obtained.

By starting with 2,6-dimethyl-4-heptanone, 3-isobutyl-5-methyl-1-hexene-3-ol having a boiling point of 87° C. under 20 mm pressure of mercury and a refractive index $n_D^{24}=1.4395$ was obtained. This compound is not described in the literature.

By starting with benzophenone, 1,1-diphenyl-2-propene-1-ol having a boiling point of 105°-110° C. under 0.04 mm pressure of mercury and a refractive index $n_D^{22}=1.593$ was obtained. This compound is not described in the literature.

By starting with 4,4-dimethyl-cyclohexane-1-one, 1-vinyl-4,4-dimethyl-cyclohexane-1-ol having a boiling point of 93°-96° C. under 20 mm pressure of mercury was obtained. This compound is not described in the literature.

By starting with 3,3,5,5-tetramethyl-cyclohexane-1-one, 3,3,5,5-tetramethyl-1-vinyl-cyclohexane-1-ol having a boiling point of 98° C. under 18 mm pressure of mercury and a refractive index $n_D^{24}=1.467$ was obtained.

By starting with 2,3,5,6-tetrahydropyrane-4-one, 2,3,5,6-tetrahydro-4-vinyl-pyrane-4-ol having a boiling point of 97°-100° C. under 21 mm pressure of mercury and a refractive index $n_D^{30}=1.473$ was obtained. This compound is not described in the literature.

By starting with cyclobutanone, 1-vinyl-cyclobutane-1-ol having a boiling point of 46°-50° C. under 17 mm pressure of mercury and a refractive index $n_D^{25}=1.4590$ was obtained. This compound is not described in the literature.

II. Preparation of 1-bromo-3-ethyl-2-pentene

A solution of 19.1 cc of phosphorus tribromide in 125 cc of petroleum ether (boiling point of 50°-70° C.) was introduced within 1 hour and at a temperature of about −20° C. into a mixture of 64 gm of 3-ethyl-1-pentene-3-ol and 190 cc of petroleum ether (boiling point=50°-70° C.). The reaction mixture was agitated for 1 hour and 30 minutes at −10° C. and then it was poured into a mixture of salt water and ice. The organic phase was decanted, washed first with an aqueous sodium bicarbonate solution and then with an aqueous sodium chloride solution. The combined aqueous phases were re-extracted with petroleum ether and the re-extractions were combined with the principal organic solution. The solution thus obtained was dried over magnesium sulfate, filtered and dried. The solvent was removed under normal pressure in the presence of potassium carbonate in an inert atmosphere in an apparatus provided with a rectifying column. The resultant residue was then rectified under reduced pressure in the presence of potassium carbonate and in an inert atmosphere to obtain 87.175 gm of 1-bromo-3-ethyl-2-pentene having a boiling point of 74° C. under 28 mm pressure of mercury. This product was utilized as such for the next step. It was maintained in an inert atmosphere in the presence of potassium carbonate. Working in the same fashion, but starting with 3-propyl-1-hexene-3-ol, 1-bromo-3-propyl-2-hexene having a boiling point of 85°-90° C. under 17 mm pressure of mercury and a refractive index $n_D^{22}=1.483$ was obtained.

By starting with 3-isopropyl-4-methyl-1-pentene-3-ol, 1-bromo-3-isopropyl-4-methyl-2-pentene having a boiling point of 92° C. under 32 mm pressure of mercury and a refractive index $n_D^{22}=1.479$ was obtained. This compound is not described in the literature.

By starting with 3-isobutyl-5-methyl-1-hexene-3-ol, 1-bromo-3-isobutyl-5-methyl-2-hexene with a boiling point of 70°-76° C. under 1 mm pressure of mercury and a refractive index $n_D^{24}=1.4750$ was obtained.

This compound is not described in the literature.

By starting with 2,6-dimethyl-1-vinyl-cyclohexane-1-ol, 1-bromo-2-(2′,6′-dimethylcyclohexylidene)-ethane having a boiling point of 115°-120° C. under 20 mm pressure of mercury was obtained. This compound is not described in the literature.

By starting with 1-vinyl-4,4-dimethylcyclohexane-1-ol, 1-bromo-2-(4′,4′-dimethylcyclohexylidene)-ethane having a refractive index $n_D^{30}=1.5060$ was obtained. This compound is not described in the literature.

By starting with 3,3,5,5-tetramethyl-1-vinyl-cyclohexane-1-ol, 1-bromo-2-(3′,3′,5′,5′-tetramethyl-cyclohexylidene)-ethane having a boiling point of 87° C. under 0.5 mm pressure of mercury and a refractive index $n_D^{25}=1.505$ was obtained.

By starting with 2,3,5,6-tetrahydro-4-vinyl-pyran-4-ol, 1-bromo-2-(2′,3′,5′,6′-tetrahydro-4′-pyranylidene)-ethane having a boiling point of 73° C. under 1.5 mm pressure of mercury and a refractive index $n_D^{25}=1.529$ was obtained. This compound is not described in the literature.

By starting with 1-vinyl-cyclobutane-1-ol, 1-bromo-2-cyclobutylidene-ethane with a boiling point of 56°-58° C. under 15 mm pressure of mercury and a refractive index $n_D^{25}=1.5160$ was obtained. This compound is not described in the literature.

By starting with 1,1-diphenyl-2-propene-1-ol, 1-bromo-3-diphenyl-2-propene having a melting point of 43° C. was obtained. This compound is not described in the literature.

III. Preparation of 3-methyl-2-cyclohexene-1-ol 8.25 gm of lithium aluminum hydride were introduced under an atmosphere of nitrogen into 100 cc of tetrahydrofuran and at a temperature of 0° C. a solution of 33 gm of 3-methyl-2-cyclohexene-1-one obtained according to the method described by KLAZE-/Ann.281,94(1894)/, in 35 cc of tetrahydrofuran were added thereto within the space of about 45 minutes. The reaction mixture was agitated at room temperature for 1 hour. The excess hydride was decomposed by addition of ethyl ether saturated with water and then by addition of water. The precipitate thus formed was eliminated by filtration and the filtrate obtained was dried over magnesium sulfate and concentrated to dryness to obtain 31.85 gm of raw 3-methyl-2-cyclohexene-1-ol which product was utilized as such for the next step. This product was a liquid with a refractive index of $n_D^{26}=1.4785$.

EXAMPLE I

Preparation of dl-trans 3,3-dimethyl-2-(2'-ethyl-1'-butenyl) cyclopropanecarboxylic acid and its ester with dl-allethrolone.

Step A: Preparation of (3-ethyl-2-pentenyl)-phenylsulfone.

1.85 gm of sodium carbonate and 18.5 gm of sodium phenyl sulfinate were introduced into 60 cc of methanol. Then 20 gm of 1-bromo-3-ethyl-2-pentene were added within the space of about 30 minutes at room temperature to the resulting suspension, which then was agitated for 1 hour and 30 minutes at room temperature. Then the reaction mixture was poured into ice-water and the organic phase was was separated by decanting. The aqueous phase was extracted with ethyl ether and the ether extracts were combined with the principal organic solution. The solution thus obtained was dried over magnesium sulfate and the solvent was removed under reduced pressure to obtain 21.665 gm of (3-ethyl-2-pentenyl)-phenylsulfone. A sample of this product was rectified under reduced pressure and the boiling point was 125° C. under 0.02 mm pressure of mercury and its refractive index $n_D^{23} = 1.530$.

Analysis: $C_{13}H_{18}SO_2$; molecular weight=238.34. Calculated: C 65.53%; H 7.61%; S 13.46%. Found: 65.4; 7.6; 13.2.

This compound is not described in the literature.

Step B: Preparation of ethyl dl-trans 3,3-dimethyl-2-(2'-ethyl-1'-butenyl)-cyclopropanecarboxylate 39 gm of potassium tert.-butylate titering 87% were dissolved in 240 cc of dimethylformamide and after 30 gm of (3-ethyl-2-pentenyl)-phenyl sulfone were introduced into this solution, it was then agitated for 15 minutes. Next, 29.1 gm of ethyl $\beta,\beta$-dimethylacrylate were introduced dropwise into the reaction mixture within the space of 10 minutes. This mixture was then agitated for 2 hours at room temperature, cooled thereafter to 0° C., and poured into a mixture of ice and a dilute aqueous solution of hydrochloric acid. Then the reaction mixture was extracted with ethyl ether and the ether solutions were combined, washed first with an aqueous solution of sodium chloride, then with an aqueous solution of sodium bicarbonate and finally again with an aqueous solution of sodium chloride. The ether solution was dried over magnesium sulfate, concentrated to dryness under reduced pressure and then rectified under reduced pressure to obtain 25.57 gm of raw ethyl dl-trans 3,3-dimethyl-2-(2'-ethyl-1'-butenyl)-cyclopropanecarboxylate having a boiling point of 70° C.-72° C. under 0.08 mm pressure of mercury and a refractive index $n_D^{23}=1.462$. This product was utilized as such for the next step.

This product is not described in the literature.

Step C: Preparation of dl-trans-3,3-dimethyl-2-(2'-ethyl 1'-butenyl)-cyclopropanecarboxylic acid 20 gm of raw ethyl dl-trans 3,3-dimethyl-2-(2'-ethyl-1'-butenyl)-cyclopropanecarboxylate were introduced into a mixture of 100 cc of a 2N methanolic sodium hydroxide solution and 20 cc of water. The reaction mixture was heated to reflux which was maintained for 1 hour. Then the methanol was eliminated under reduced pressure and the remainder was diluted with water. The aqueous phase was extracted with ethyl ether and the ether extracts were combined. The ether solution thus obtained was washed once with water. The aqueous wash waters were combined with the principal aqueous phase, and all of the aqueous phases combined were acidified with a dilute aqueous solution of hydrochloric acid. The acidified aqueous phase was extracted with methylene chloride and the methylene chloride solution is washed with water, dried over magnesium sulfate and concentrated to dryness under reduced pressure. The residual oil was rectified under reduced pressure to obtain 11.95 gm of dl-trans 3,3-dimethyl-2-(2'-ethyl-1'-butenyl)-cyclopropanecarboxylic acid having a boiling point of 110° C. under 0.05 mm of mercury pressure and melting point 36°-37° C. A sample of this product, purified by rectification under reduced pressure, had a boiling point=94° C. under 0.01 mm pressure of mercury and a melting point=37° C.

Analysis: $C_{12}H_{20}O_2$; molecular weight=196.28. Calculated: C 73.42%; H 10.27%. Found: 73.5; 10.0.

This product is not described in the literature.

Step D: Preparation of dl-trans 3,3-dimethyl-2-(2'-ethyl-1'-butenyl)-cyclopropanecarboxylic acid chloride.

5 gm of dl-trans 3,3-dimethyl-2-(2'-ethyl-1'-butenyl)-cyclopropanecarboxylic acid were introduced into 10 cc of petroleum ether (boiling point=50°-70° C.) and after 2.8 cc of thionyl chloride were added, the mixture was agitated at room temperature for 1 hour and 30 minutes. The petroleum ether and excess thionyl chloride were eliminated by distillation and the residue was rectified under reduced pressure to obtain 5.25 gm of dl-trans 3,3-dimethyl-2-(2'-ethyl-1'-butenyl)-cyclopropanecarboxylic acid chloride having a boiling point of 68° C. under 0.2 mm pressure of mercury. This product was utilized as such for the next step.

This product is not described in the literature.

Step E: Preparation of dl-trans 3,3-dimethyl-2-(2'-ethyl-1'-butenyl)-cyclopropanecarboxylate of dl-allethrolone 5.25 gm of dl-trans 3,3-dimethyl-2-(2'-ethyl-1'-butenyl)-cyclopropanecarboxylic acid chloride were introduced into a mixture of 30 cc of benzene and 6 cc of pyridine. Then a solution of 3.7 gm of dl-allethrolone in 5 cc of benzene was added over about 10 minutes and at a temperature of 0° C. The reaction mixture was agitated for about 15 hours at room temperature, after which the pyridine hydrochloride formed was eliminated by filtration. The organic phase was washed first with a dilute aqueous hydrochloric acid solution, then with water, next with an aqueous sodium bicarbonate solution and finally again with water. The solution thus obtained was dried over magnesium sulfate and then concentrated to dryness under reduced pressure. The recovered residue was subjected to chromatography through alumina with elution with cyclohexane to obtain 5.445 gm of dl-trans 3,3-dimethyl-2-(2'-ethyl-1'-butenyl)-cyclopropanecarboxylate of dl-allethrolone having a refractive index of $n_D^{22}=1.4520$.

Analysis: $C_{21}H_{30}O_3$; molecular weight=330.45. Calculated: C 76.32%; H 9.15%. Found: 76.1; 9.0.

This product is not described in the literature.

EXAMPLE II

Preparation of dl-trans 3,3-dimethyl-2-(2'-isobutyl-4'-methyl-1'-pentenyl)-cyclopropanecarboxylic acid and its ester with dl-allethrolone

Step A: Preparation of (3-isobutyl-5-methyl-2-hexenyl)-phenyl-sulfone 55 gm of sodium phenyl sulfinate were dissolved in 500 cc of methanol and then 8 gm of potassium carbonate, 1 gm of sodium iodide and finally 71 gm of 1-bromo-3-isobutyl-5-methyl-2-hexane were added to the solution, which was then agitated for 15 hours at room temperature. Thereafter, the reaction mixture was concentrated to dryness under reduced pressure and water was added thereto. The aqueous phase was extracted with methylene chloride and the methylene chloride extracts were combined. The organic solution thus obtained was washed with water, dried and concentrated to dryness under reduced pressure. The residue was subjected to chromatography through an alumina column to obtain 62.32 gm of the (3-isobutyl-5-methyl-2-hexenyl)phenylsulfone. This product is not described in the literature.

Step B: Preparation of methyl dl-trans 3,3-dimethyl-2-(2'-isobutyl-4'-methyl-1'-pentenyl)-cyclopropanecarboxylate.

24.56 gm of potassium tert-butylate titering 87% were dissolved in 120 cc of dimethylformamide and 28 gm of (3-isobutyl-5-methyl-2-hexenyl) phenyl sulfone were added. The solution was agitated for 2 minutes and then 18 cc of methyl $\beta,\beta$-dimethylacrylate were introduced therein within about 10 minutes. The reaction mixture was agitated for 2 hours at room temperature, then poured into a mixture of a dilute aqueous hydrochloric acid solution and water. The aqueous phase was extracted with methylene chloride and the methylene chloride extracts were combined and was successively washed with water, with an aqueous solution of sodium bicarbonate and again with water, then dried and concentrated to dryness. The resultant residue was rectified under reduced pressure to obtain 24.68 gm of the desired methyl dl-trans 3,3-dimethyl-2-(2'-isobutyl-4'-methyl-1'-pentenyl)-cyclopropanecarboxylate, having a boiling point of 113° C. under 1 mm pressure of mercury.

This product is not described in the literature.

Step C: Preparation of dl-trans 3,3-dimethyl-2-(2'-isobutyl-4'-methyl-1'-pentenyl)-cyclopropanecarboxylic acid.

18 cc of a 10 N aqueous sodium hydroxide solution were introduced into a mixture of 100 cc of methanol and 10 cc of water. The solution was then brought to reflux under a current of nitrogen and reflux was maintained for 10 minutes after which a solution of 24.6 gm of methyl dl-trans 3,3-dimethyl-2-(2'-isobutyl-4'-methyl-1'-pentenyl)-cyclopropanecarboxylate in 30 cc of methanol was added. The reaction mixture was agitated for 1 hour at reflux after which water was added and the methanol was eliminated. Then the reaction mixture was cooled and the aqueous phase was extracted with ethyl ether. The ether extracts were combined and washed with water. The wash waters were combined with the principal aqueous phase and the ether solution containing the neutral fraction was eliminated.

The combined aqueous phase were acidified with a dilute aqueous hydrochloric acid solution and the acid aqueous phase was extracted with ether. The ether extracts were combined, washed with water, dried and concentrated to dryness. The residue obtained was crystallized from petroleum ether, (boiling point=3-5°-70° C.) and then from a mixture of isopropyl ether and petroleum ether, (boiling point=35°-70° C.) to obtain the desired dl-trans-3,3-dimethyl-2-(2'-isobutyl)-4'-methyl-1'-pentenyl)-cyclopropanecarboxylic acid having a melting point 74° C.

Analysis: $C_{16}H_{28}O_2$; molecular weight=252.38. Calculated: C 76.14%; H 11.18%. Found: 76.1; 10.9.

This product is not described in the literature.

Step D: Preparation of dl-trans 3,3-dimethyl-2-(2'-isobutyl-4'-methyl-1'-pentenyl)-cyclopropanecarboxylic acid chloride.

8 gm of dl-trans 3,3-dimethyl-2-(2'-isobutyl-4'-methyl-1'-pentenyl)-cyclopropane carboxylic acid were dissolved under an atmosphere of nitrogen in 25 cc of petroleum ether (boiling point=35°-70° C.) and then, 3.5 cc of thionyl chloride were slowly added. The solution was agitated first for 1 hour and 30 minutes at room temperature, then for 30 minutes at 40° C. The reaction solution was concentrated to dryness under reduced pressure and then rectified to obtain 7.4 gm of the desired dl-trans 3,3-dimethyl-2-(2'-isobutyl-4'-methyl-1'-pentenyl)-cyclopropanecarboxylic acid chloride having a boiling point of 118° C. under 1.5 mm pressure of mercury and a refractive index $n_D^{23}=1.4775$. The product was utilized as such for the next step.

This product is not described in the literature.

Step E: Preparation of dl-trans 3,3-dimethyl-2-(2'-isobutyl-4'-methyl-1'-pentenyl)-cyclopropanecarboxylate of dl-allethrolone.

Under an atmosphere of nitrogen, 7.335 gm of dl-trans 3,3-dimethyl-2-(2'-isobutyl-4'-methyl-1'-pentenyl)-cyclopropane carboxylic acid chloride were introduced into 20 cc of benzene and after a solution of 4 gm of dl-allethrolone in a mixture of 8 cc of pyridine and 20 cc of benzene was added at 10° C., the reaction solution was agitated for 15 hours at room temperature. Thereafter, first 1 cc of formic acid and then water was added. The aqueous phase was extracted with ethyl ether and the ether extracts were combined, successively washed with a dilute aqueous solution of hydrochloric acid, with an aqueous solution of sodium bicarbonate and finally with water, and then dried and concentrated to dryness.

The resultant residue was dissolved in benzene and the benzene solution was passed through an alumina column, then it was again concentrated to dryness. The residue was rectified under reduced pressure to obtain 4.9 gm of the desired dl-trans 3,3-dimethyl-2-(2'-isobutyl-4'-methyl-1'-pentenyl)-cyclopropanecarboxylate of dl-allethrolone having a boiling point of 160° C. under 0.07 mm pressure of mercury and a refractive index $n_D^{23}=1.4950$.

Analysis: $C_{25}H_{38}O_3$; molecular weight=386.55. Calculated: C 77.67%; H 9.91%. Found: 77.9; 9.7.

Ultra-Violet Spectra (in ethanol)

$\lambda$ max.: 225 m$\mu$ ($\epsilon$=20,300) This product is not described in the literature.

EXAMPLE III

Preparation of dl-trans 3,3-dimethyl-2-(2',2'-diphenylvinyl)-cyclopropanecarboxylic acid and its ester with dl-allethrolone

Step A: Preparation of (3,3-diphenyl-2-propenyl)-phenylsulfone 15.5 gm of sodium phenyl sulfinate and 1.5 gm of sodium carbonate were introduced into 80 cc of methanol. Then 25.6 gm of 1-bromo-3,3-diphenyl-2-propene were added to the reaction mixture under an atmosphere of nitrogen and at room temperature which was then agitated for 1 hour and 30 minutes. Next, the reaction mixture was poured into cold water and extracted with methylene chloride. The methylene chloride extracts were combined, washed with water, dried and concentrated to dryness. The residue was partly crystallized. The precipitate formed was isolated by vacuum filtering and dried to obtain 25.48 gm of (3,3-diphenyl-2-propenyl)-phenyl sulfone having a melting point of 104° C. A sample of this product, recrystallised from isopropyl ether, had a melting point of 106° C.

Analysis: $C_{21}H_{18}SO_2$; molecular weight=334.43 Calculated: C 75.41%; H 5.42%; S 9.58%. Found: 75.3; 5.4; 9.4.

This product is not described in the literature.

Step B: Preparation of ethyl dl-trans 3,3-dimethyl-2-(2',2'-diphenylvinyl)-cyclopropanecarboxylate Under an atmosphere of nitrogen, 21.6 gm of potassium tert.butylate titering 87% and 28.08 gm of (3,3-diphenyl-2-propenyl) phenyl sulfone were introduced into 150 cc of dimethylsulfoxide and the mixture was agitated for 30 minutes at 105° C. Then 17.5 cc of ethyl $\beta,\beta$-dimethyl-acrylate were added and the reaction mixture was agitated for 2 hours, followed by addition of 17.5 cc more of ethyl $\beta,\beta$-dimethylacrylate and the mixture was agitated for 7 hours at 105° C. Thereafter the reaction mixture was cooled to 0° C. and acidified with a dilute aqueous solution of hydrochloric acid. The aqueous phase was extracted with methylene chloride and the methylene chloride extracts were combined; washed first with an aqueous solution of sodium bicarbonate, then with water, then dried and concentrated to dryness. The partly crystallized residue was filtered to eliminate any impurity. The filtrate was subjected to chromatography through alumina with elution with cyclohexane to obtain the desired ethyl dl-trans 3,3-dimethyl-2-(2',2'-diphenylvinyl)-cyclopropanecarboxylate which was used as such for the next step.

This product is not described in the literature.

Step C: Preparation of dl-trans 3,3-dimethyl-2-(2',2'-diphenylvinyl)-cyclopropanecarboxylic acid 42.7 cc of a 2 N methanolic sodium hydroxide solution were introduced into 100 cc of methanol and 10 cc of water, followed by 18.45 gm of ethyl dl-trans 3,3-dimethyl-2-(2',2'-diphenylvinyl)-cyclopropanecarboxylate were added thereto. The mixture was brought to reflux and maintained there for 1 hour and 30 minutes. The methanol was removed by distillation and water was added. Next the aqueous phase was extracted with ethyl ether to eliminate the neutral fraction and the combined ether extracts were washed with water and the wash water was combined with the principal aqueous phase. Then the entire aqueous phase was acidified with a dilute aqueous solution of hydrochloric acid which was then repeatedly extracted with methylene chloride; the methylene chloride solutions were combined, washed with water, dried and concentrated to dryness to obtain 7.95 gm of dl-trans 3,3-dimethyl-2-(2',2'-diphenylvinyl)-cyclopropanecarboxylic acid having a melting point of 115° C. A sample of this product crystallized from a mixture of isopropyl ether and petroleum ether, had a melting point of 115° C.

Analysis: $C_{20}H_{20}O_2$; molecular weight=292.36 Calculated: C 82.15%; H 6.89%. Found: 82.1; 7.0.

According to its N.M.R. spectra, this product consisted of the trans derivative containing about 10% of the cis derivative. This product is not described in the literature.

Step D: Preparation of dl-trans 3,3-dimethyl-2-(2',2'-diphenylvinyl)-cyclopropanecarboxylic acid chloride 2.5 gm of dl-trans 3,3-dimethyl-2-(2',2'-diphenylvinyl)-cyclopropanecarboxylic acid were introduced into 10 cc of benzene and after the addition of 0.9 cc of thionyl chloride, the mixture was maintained at room temperature for 20 minutes, then heated to 100° C. and maintained at this temperature for 3 hours. Excess benzene and thionyl chloride were eliminated by distillation under vacuum. The raw-dl-trans 3,3-dimethyl-2-(2',2'-diphenylvinyl)-cyclopropanecarboxylic acid chloride thus obtained in a quantitative yield was utilized as such for the next step.

This product is not described in the literature.

Step E: Preparation of dl-trans 3,3-dimethyl-2-(2',2'-diphenylvinyl)-cyclopropanecarboxylate of dl-allethrolone The raw dl-trans 3,3-dimethyl-2-(2',2'-diphenylvinyl)-cyclopropanecarboxylic acid chloride (corresponding to 2.5 gm of acid) was introduced into 13 cc of benzene and 1.2 cc of pyridine and 1.3 gm of dl-allethrolone were added thereto. The reaction mixture was agitated for about 15 hours at room temperature. The precipitate formed was eliminated by filtration and the benzene filtrate was washed first with a dilute aqueous solution of hydrochloric acid, then with water, then with an aqueous solution of sodium bicarbonate and lastly again with water. Next the benzene solution was dried and concentrated to dryness. The residue was subjected to chromatography through alumina with elution with benzene to obtain 2.034 gm of di-trans 3,3-dimethyl-2-(2',2'-diphenylvinyl)-cyclopropanecarboxylate of dl-allethrolone having a refractive index $n_D^{44}=1.569$.

Analysis: $C_{29}H_{30}O_3$; molecular weight=426.53. Calculated: C 81.66%; H 7.09%. Found: 81.9; 7.2.

| Ultra-Violet Spectra | (in ethanol) | |
| --- | --- | --- |
| λ max.: | 227 mµ | ($\epsilon$ = 28,100) |
| λ max.: | 262 mµ | ($\epsilon$ = 17,050) |

This product is not described in the literature.

EXAMPLE IV

Preparation of dl-trans 3,3-dimethyl-2-cyclopentylidene-methyl-cyclopropanecarboxylic acid and its ester with dl-allethrolone

Step A: Preparation of (2-cyclopentylidene-ethyl)-phenyl sulfone 22.3 gm of sodium phenyl sulfinate, 2.2 gm of potassium carbonate and 0.2 gm of sodium iodide were introduced into 50 cc of methanol. Then 23.6 gm of 1-bromo-2-cyclopentylidene-ethane were added at a temperature of about +10° C. and under agitation and the reaction mixture was agitated for 2 hours at 20° C. Thereafter, the reaction mixture was poured into ice water and cooled to 0° C. The precipitate formed was isolated by vacuum filtering and dried under vacuum in the presence of potassium hydroxide to obtain 15 gm of (2-cyclopentylidene-ethyl)-phenyl sulfone having a melting point of 68° C. A sample of the product crystallized from isopropyl ether had a melting point of 68° C.

Analysis: $C_{13}H_{16}SO_2$; molecular weight=236.33. Calculated: C 66.06%; H 6.82%; S 13.57%. Found: 65.8; 6.8; 13.2.

This product is not described in the literature.

The 1-bromo 2-cyclopentylidene-ethane was prepared according to the process described in Bull. Soc. Chim. 1964, pg. 2618.

Step B: Preparation of ethyl dl-trans 3,3-dimethyl-2-cyclopentylidene-methyl-cyclopropanecarboxylate Under an atmosphere of nitrogen, first 16.5 gm of potassium ter.-butylate titering 87%, then 15 gm of (2-cyclopentylidene-ethyl)phenyl sulfone were introduced into 100 cc of dimethylformamide. The mixture was agitated for 10 minutes and then 16 cc of ethyl $\beta,\beta$-dimethylacrylate were added over about 10 minutes and the reaction mixture was agitated for 3 hours. Thereafter, the reaction mixture was cooled to 0° C. and poured into a dilute aqueous solution of hydrochloric acid. The aqueous phase was extracted with methylene chloride, the methylene chloride extracts were combined, washed first with a dilute aqueous solution of sodium bicarbonate, then with water, then dried and concentrated to dryness under reduced pressure. The resultant residue was rectified under reduced pressure to obtain 12.28 gm of raw ethyl dl-trans 3,3-dimethyl-2-cyclopentylidene-methyl-cyclopropanecarboxylate having a boiling point of 88° C. under 0.05 mm pressure of mercury, and it was utilized as such for the following step.

This product is not described in the literature.

Step C: Preparation of dl-trans 3,3-dimethyl-2-cyclopentylidene-methyl-cyclopropanecarboxylic acid Under an atmosphere of nitrogen, 12.28 gm of raw ethyl dl-trans 3,3-dimethyl-2-cyclopentylidene-methyl-cyclopropanecarboxylate were introduced into a mixture consisting of 32 cc of a 2 N methanolic sodium hydroxide solution, 5 cc of water and 5 cc of methanol. The reaction mixture was refluxed for 1 hour and 30 minutes, then cooled to room temperature and a water-ice mixture was added. Next, the aqueous phase was extracted with ethyl ether to eliminate the neutral fractions and the combined ether extracts were washed with water. The aqueous wash waters were combined with the principal aqueous phase which was then acidified with a dilute aqueous solution of hydrochloric acid. Then the acidified aqueous phase was extracted with methylene chloride and the methylene chloride extracts were combined, washed with water, dried and concentrated to dryness under reduced pressure. The residue was rectified under vacuum to obtain 5.27 gm of dl-trans 3,3-dimethyl-2-cyclopentylidene-methyl-cyclopropanecarboxylic acid having a boiling point of 115° C. under 0.1 mm pressure of mercury and a melting point of 59° C.

Analysis: $C_{12}H_{18}O_2$; molecular weight=194.26. Calculated: C 74.19%; H 9.34%. Found: 74.1; 9.3. This product is not described in the literature.

Step D: Preparation of dl-trans 3,3-dimethyl-2-cyclopentylidene-methyl-cyclopropanecarboxylic acid chloride Under an atmosphere of nitrogen, 2.5 gm of dl-trans 3,3-dimethyl-2-cyclopentylidene-methyl-cyclopropanecarboxylic acid were introduced into 10 cc of benzene and 1.04 cc of thionyl chloride were added within about 30 minutes and under agitation and the reaction mixture was agitated for 1 hour at room temperature. The excess benzene and thionyl chloride were eliminated by distillation and the residue was rectified under reduced pressure to obtain 2.2 gm of raw dl-trans 3,3-dimethyl-2-cyclopentylidene-methyl-cyclopropanecarboxylic acid chloride having a boiling point of 82° C. under 0.25 mm pressure of mercury and it was utilized as such for the next step.

This product is not described in the literature.

Step E: Preparation of dl-trans 3,3-dimethyl-2cyclopentylidene-methyl-cyclopropanecarboxylate of dl-allethrolone Under an atmosphere of nitrogen, 2.2 gm of dl-trans 3,3-dimethyl-2-cyclopentylidene-methyl-cyclopropanecarboxylic acid chloride and 2 cc of pyridine were introduced into 15 cc of anhydrous benzene. 1.75 gm of dl-allethrolone dissolved in 5 cc of benzene were added over about 10 minutes and the mixture was agitated for about 15 hours at room temperature. The precipitate formed was eliminated by filtration and the benzene filtrate was washed first with salt water, then with a dilute aqueous solution of hydrochloric acid and again with salt water. The aqueous phases were extracted with ether and the ether extracts were combined with the benzene solution. The organic solution thus obtained was dried and concentrated to dryness. The residue was subjected to chromatography through an alumina column with elution with benzene and methylene chloride to obtain 3.015 gm of dl-trans 3,3-dimethyl-2-cyclopentylidene-methylcy-clopropanecarboxylate of dl-allethrolone having a refractive index $n_D^{20}=1.5195$.

Ultraviolet Spectra (in ethanol)

$\lambda$max.: 225–226 m$\mu$ ($\epsilon$=20,700)

Analysis: $C_{21}H_{28}O_3$; molecular weight=328.43. Calculated: C 76.79%; H 8.59%. Found: 76.6; 8.4.

This product is not described in the literature.

EXAMPLE V

Preparation of dl-trans 3,3-dimethyl-2-cyclohexylidenemethyl-cyclopropanecarboxylic acid and its ester with dl-allethrolone

Step A: Preparation of (2-cyclohexylidene-ethyl)-phenyl sulfone

First, 38.5 gm of sodium phenyl sulfinato and then 3.85 gm of sodium carbonate were introduced into 116 cc of methanol and 44 gm of freshly prepared 1-bromo-2-cyclohexylidene-ethane were added dropwise over 30 minutes and at room temperature. The reaction mixture was then agitated for 1 hour and 30 minutes at room temperature after which the reaction mixture was poured into 400 cc of ice water. The precipitate formed was vacuum filtered, washed with water and dried. The raw product thus obtained was dissolved at high temperature in a mixture consisting of methylene chloride and methanol. The solution obtained was dried over magnesium sulfate, concentrated to a small volume and admixed with isopropyl ether. The precipitate formed was vacuum filtered and dried to obtain 36.4 gm of (2-cyclohexylidene-ethyl)-phenyl sulfone, having a melting point of 70° C. A sample of this product, crystallized from isopropyl ether, had a melting point of 70° C.

Analysis: $C_{14}H_{18}SO_2$; molecular weight=250.35. Calculated: C 67.16%; H 7.24%; S 12.81%. Found: 67; 7.1; 12.5.

This product is not described in the literature.

The 1-bromo-2-cyclohexylidene-ethane was prepared according to the process described in Helv. (1942), vol. 25, pg. 29.

Step B: Preparation of ethyl dl-trans 3,3-dimethyl-2-cyclohexylidene-methyl-cyclopropanecarboxylate 20.6 gm of potassium tert.-butylate titering 87% were introduced into 120 cc of dimethylformamide and then 20 gm of (2-cyclohexylidene-ethyl)-phenyl sulfone were added thereto. After 10 minutes, 17.3 cc of ethyl $\beta,\beta$-dimethylacrylate were added and the mixture was agitated for 1 hour at room temperature. Thereafter, the reaction mixture was cooled to about +5° C., acidified with a dilute aqueous solution of hydrochloric acid and the aqueous phase was extracted with methylene chloride.

The methylene chloride solution obtained was washed first with an aqueous solution of sodium bicarbonate, then with water, dried over magnesium sulfate and concentrated to dryness under reduced pressure to obtain 22.75 gm of ethyl dl-trans 3,3-dimethyl-2-cyclohexylidene-methyl-cyclopropanecarboxylate which was utilized as such for the next step.

This product is not described in the literature.

Step C: Preparation of dl-trans 3,3-dimethyl-2-cyclohexylidene-methyl-cyclopropanecarboxylic acid 22.75 gm of ethyl dl-trans 3,3-dimethyl-2-cyclohexylidene-methyl-cyclopropanecarboxylate were introduced into a mixture consisting of 70 cc of a 2 N methanolic sodium hydroxide solution, 2.5 cc of water and 25 cc of methanol. The reaction mixture was heated to reflux and maintained at reflux for 45 minutes. Thereafter, the methanol was removed under reduced pressure and water was added to the residue. The insoluble matter formed (the sodium salt of the desired acid) was vacuum filtered, then washed first with water, then with ether, and these washwaters were eliminated. The said product was agitated with 100 cc of a dilute aqueous solution of hydrochloric acid and 100 cc of methylene chloride until total dissolution had been attained. The organic phase was then separated by decanting and it was washed with water. The wash waters were extracted with methylene chloride. The said methylene chloride extracts were combined with the principal methylene chloride solution, dried over magnesium sulfate and finally concentrated to dryness under reduced pressure. The residue thus obtained was admixed with petroleum ether and the precipitate formed was vacuum filtered, washed with petroleum ether and dried to obtain the desired dl-trans 3,3-dimethyl-2-cyclohexylidene-methyl-cyclopropane carboxylic acid, having a melting point of 88°–89° C.

Analysis: $C_{13}H_{20}O_2$; molecular weight=208.29. Calculated: C 74.96%; H 9.67%. Found: 75.1; 9.4.

This product is not described in the literature.

Step D: Preparation of dl-trans 3,3-dimethyl-2-cyclohexylidene-methyl-cyclopropanecarboxylic acid chloride.

3 gm of dl-trans 3,3-dimethyl-2-cyclohexylidene-methyl-cyclopropanecarboxylic acid were introduced into 15 cc of petroleum ether (boiling point=50°–70° C.) and then 1.55 cc of thionyl chloride were added over about 30 minutes, and the mixture was agitated at room temperature for about 1 hour. Thereafter, the petroleum ether was eliminated under reduced pressure and the raw acid chloride was rectified under reduced pressure to obtain 2.66 gm of the desired dl-trans 3,3-dimethyl-2-cyclohexylidene-methyl-cyclopropanecarboxylic acid chloride having a boiling point of 88°–90° C. under 0.35 mm pressure of mercury and was utilized as such for the next step. This product occurred in liquid form at room temperature. This compound is not described in the literature.

Step E: Preparation of dl-trans 3,3-dimethyl-2-cyclohexylidene-methyl-cyclopropanecarboxylate of dl-allethrolone 1.56 gm of dl-trans 3,3-dimethyl-2-cyclohexylidene-methyl-cyclopropanecarboxylic acid chloride were introduced into a mixture of 15 cc of benzene and 1.9 cc of pyridine. Then a solution of 1.050 gm of dl-allethrolone in 5 cc of benzene was added dropwise within a few minutes and the mixture was agitated for about 15 hours at room temperature. Thereafter, the precipitate formed was vacuum filtered and the resultant filtrate was washed successively with a dilute aqueous solution of hydrochloric acid, with an aqueous solution of sodium chloride, with an aqueous solution of sodium bicarbonate and finally again with an aqueous solution of sodium chloride. The aqueous wash waters were combined and extracted with benzene. The benzene extract was combined with the principal benzene solution and the entire benzene solution was then dried over magnesium sulfate and concentrated to dryness under reduced pressure. The recovered residue was purified by chromatography through alumina with elution with cyclohexane to obtain 1.500 gm of dl-trans 3,3-dimethyl-2-cyclohexylidene-methyl-cyclopropanecarboxylate of dl-allethrolone having a refractive index $n_D^{27}=1.515$.

Analysis: $C_{22}H_{30}O_3$; molecular weight=342.46. Calculated: C=77.15%; H 8.82%. Found: 77.4; 9.0.

Ultraviolet Spectra (in ethanol)

λmax.: 223 mμ (ε=19,500)

This product is not described in the literature.

EXAMPLE VI

Preparation of dl-trans 3,3-dimethyl-2-(2'-propyl-1'-pentenyl)-cyclopropanecarboxylic acid and its dl-allethrolone ester Using the procedure of Example I, 1-bromo-3-propyl-2-hexene was reacted with sodium phenyl sulfinate to form (3-propyl-2-hexenyl)-phenyl sulfone which was then reacted with ethyl β,β-dimethyl-acrylate to form ethyl dl-trans 3,3-dimethyl-2-(2'-propyl-1'-pentenyl)-cyclopropanecarboxylate having a boiling point of 80° C. at 0.06 mm Hg and a refractive index $n_D^{22}$=1.464. The said ethyl ester was hydrolyzed under alkaline conditions to form dl-trans 3,3-dimethyl-2-(2'-propyl-1'-pentenyl)-cyclopropane carboxylic acid having a boiling point of 116° C. at 0.05 mm Hg and a refractive index $n_D^{22}$=1.4755 which was then reacted with thionyl chloride to obtain dl-trans 3,3-dimethyl-2-(2'-propyl-1'-pentenyl)-cyclopropanecarboxylic acid chloride having a boiling point of 75° C. at 0.04 mm Hg and a refractive index $n_D^{24}$=1.4795.

The said acid chloride was then reacted with dl-allethrolone to form dl-trans 3,3-dimethyl-2-(2'-propyl-1'-pentenyl)-cyclopropanecarboxylate of dl-allethrolone having a refractive index $n_D^{22}$=1.499.

EXAMPLE VII

Preparation of dl-trans 3,3-dimethyl-2-(2'-isopropyl-3'-methyl-1'-butenyl)-cyclopropanecarboxylic acid and its dl-allethrolone ester Using the procedure of Example I, 1-bromo-3-isopropyl-4-methyl-2-pentene was reacted with sodium phenyl sulfinate to form (3-isopropyl-4-methyl-2-pentenyl)-phenyl sulfone having a melting point of 50° C. which was then reacted with ethyl β,β-dimethylacrylate to form ethyl dl-trans 3,3-dimethyl-2-(2'-isopropyl-3'-methyl-1'-butenyl)-cyclopropanecarboxylate. The said ethyl ester was hydrolyzed under alkaline conditions to form dl-trans 3,3-dimethyl-2-(2'-isopropyl-3'-methyl-1'-butenyl)-cyclopropane carboxylic acid having a melting point of 135° C. which was then reacted with thionyl chloride to form dl-trans 3,3-dimethyl-2-(2'-isopropyl-3'-methyl-1'-butenyl)-cyclopropanecarboxylic acid chloride having a boiling point of 78° to 80° C. at 0.1 mm Hg.

The said acid chloride was then reacted with dl-allethrolone to form dl-trans 3,3-dimethyl-2-(2'-isopropyl-3'-methyl-1'-butenyl)-cyclopropanecarboxylate of dl-allethrolone having a refractive index $n_D^{24}$=1.497.

EXAMPLE VIII

Preparation of dl-trans, 3,3-dimethyl-2-(2', 6'-dimethylcyclohexylidene-methyl)-cyclopropanecarboxylic acid and its dl-allethrolone ester Using the procedure of Example I, 1-bromo-2-(2',6'-dimethyl-cyclohexylidene)-ethane was reacted with sodium phenyl sulfinate to form [2-(2',6'-dimethylcyclohexylidene)-ethyl]-phenyl sulfone having a melting point of 96° C. which was then reacted with ethyl β,β-dimethylacrylate to form ethyl dl-trans 3,3-dimethyl-2-(2',6'-dimethyl-cyclohexylidene-methyl)-cyclopropanecarboxylate having a boiling point of 105°–110° C. at 0.5 mm Hg. The said ethyl ester was then hydrolyzed under alkaline conditions to form dl-trans 3,3-dimethyl-2-(2', 6'-dimethyl-cyclohexylidene-methyl)-cyclopropanecarboxylic acid having a boiling point of 123°–125° C. at 0.1 mm Hg and a melting point of 96° C. which was then reacted with thionyl chloride to form dl-trans 3,3-dimethyl-2-(2',6'-dimethyl-cyclohexylidene-methyl)-cyclopropanecarboxylic acid chloride having a boiling point of 104° C. at 0.5 mm Hg and a refractive index $n_D^{25}$=1.5020.

The said acid chloride was then reacted with dl-allethrolone to form dl-trans 3,3-dimethyl-2-(2',6'-dimethyl-cyclohexylidene-methyl)-cyclopropane-carboxylate of dl-allethrolone having a refractive index $n_D^{23}$=1.5136.

EXAMPLE IX

Preparation of dl-trans, 3,3-dimethyl-2-(4', 4'-dimethyl-cyclohexylidene-methyl)-cyclopropanecarboxylic acid and its dl-allethrolone ester Using the procedure of Example I, 1-bromo-2-(4',4'-dimethyl-cyclohexylidene)-ethane was reacted with sodium phenyl sulfinate to form [2-(4',4'-dimethylcyclohexylidene) ethyl]-phenyl sulfone having a melting point of 110° C. which was then reacted with methyl β,β-dimethylacrylate to form methyl dl-trans 3,3-dimethyl-2-(4',4'-dimethyl-cyclohexylidene-methyl)-cyclopropanecarboxylate having a boiling point of 120° C. at 1 mm Hg. The said methyl ester was hydrolyzed under alkaline conditions to form dl-trans 3,3-dimethyl-2-(4',4'-dimethyl-cyclohexylidene-methyl)-cyclopropane carboxylic acid having a melting point of 96° C. which was then reacted with thionyl chloride to form dl-trans 3,3-dimethyl-2-(4',4'-dimethyl-cyclohexylidene-methyl)-cyclopropane carboxylic acid chloride having a boiling point of 115° C. at 0.7 mm Hg and a refractive index $n_D^{28}$=1.5005.

The said acid chloride was then reacted with dl-allethrolone to form dl-trans 3,3-dimethyl-2-(4',4'-dimethylcyclohexylidene-methyl)-cyclopropanecarboxylate of dl-allethrolone having a refractive index $n_D^{25}$=1.5110.

EXAMPLE X

Preparation of dl-trans 3,3-dimethyl-2-(3',3',5',5'-tetramethyl-cyclohexylidene-methyl)-cyclopropane carboxylic acid and its dl-allethrolone ester Using the procedure of Example I, 1-bromo-2-(3',3',5',5'-tetramethyl-cyclohexylidene)-ethane was reacted with sodium phenyl sulfinate to form [2-(3',3',5',5'-tetramethyl-cyclohexylidene)-ethyl]-phenyl sulfone having a melting point of 55° C. which was then reacted with ethyl β,β-dimethylacrylate to form ethyl dl-trans 3,3-dimethyl-2-(3',3',5',5'-tetramethyl-cyclohexylidene methyl)-cyclopropane carboxylate. The said ethyl ester was then hydrolyzed under alkaline conditions to form dl-trans 3,3-dimethyl-2-(3',3',5',5'-tetramethyl-cyclohexylidene-methyl)-cyclopropanecarboxylic acid having a melting point of 116° C. which was then reacted with thionyl chloride to form dl-trans 3,3-dimethyl-2-(3',3',5',5'-tetramethyl-cyclohexylidene-methyl)-cyclopropanecarboxylic acid chloride having a boiling point of 119° C. at 0.8 mm Hg and a refractive index $n_D^{25}$=1.499.

The said acid chloride was then reacted with dl-allethrolone to form dl-trans 3,3-dimethyl-2-(3',3',5',5'-tetramethyl-cyclohexylidene-methyl)-cyclopropanecarboxylate of dl-allethrolone.

EXAMPLE XI

Preparation of dl-trans 3,3-dimethyl-2-(2',3',5',6'-tetrahydro-4'-pyranylidene-methyl)-cyclopropanecarboxylic acid and its dl-allethrolone ester Using the procedure of Example I, 1-bromo-2-(2',3',5',6'-tetrahydro-4-pyranylidene)-ethane was reacted with sodium phenyl sulfinate to form [2-(2',3',5',6'-tetrahydro-4'-pyranylidene)-ethyl]-phenyl sulfone having a melting point of 68° C. which was then reacted with ethyl β,β-dimethylacrylate to form ethyl dl-trans 3,3-dimethyl-2-(2',3',5',6'-tetrahydro-4'-pyranylidene-methyl)-cyclopropane carboxylate. The said ethyl ester was then hydrolyzed under alkaline conditions to form dl-trans 3,3-dimethyl-2-(2',3',5',6'-tetrahydro-4'-pyranylidene-methyl)-cyclopropanecarboxylic acid having a melting point of 102°–103° C. which was then reacted with thionyl chloride to form dl-trans 3,3-dimethyl-2-(2',3',5',6'-tetrahydro-4'-pyranylidene-methyl)-cyclopropanecarboxylic acid chloride having a boiling point of 82° C. at 0.1 mm Hg.

The acid chloride was then reacted with dl-allethrolone to form dl-trans 3,3-dimethyl-2-(2',3',5',6'-tetrahydro-4'-pyranylidene-methyl)-cyclopropanecarboxylate of dl-allethrolone having a refractive index $n_D^{25}=1.520$.

EXAMPLE XII

Preparation of 3-phenyl-2-(1'-isobutenyl)-cyclopropanecarboxylic acid and its dl-allethrolone ester Using the procedure of Example I, (3-methyl-2-butenyl)-phenyl sulfone produced as in French Pat. No. 1,483,715 was reacted with ethyl cinnamate to form ethyl 3-phenyl-2-(1'-isobutenyl)-cyclopropanecarboxylate which was hydrolyzed under alkaline conditions to form 3-phenyl-2-(1'-isobutenyl)-cyclopropanecarboxylic acid having a melting point of 104° C.

The said acid was reacted with thionyl chloride to form 3-phenyl-2-(1'-isobutenyl)-cyclopropanecarboxylic acid chloride having a boiling point of 101° to 103° C. at 0.3 mm Hg and a refractive index $n_D^{23}=1.5522$ which was then reacted with dl-allethrolone to form 3-phenyl-2-(1'-isobutenyl)-cyclopropanecarboxylate of dl-allethrolone having a refractive index $n_D^{24}=1.5487$.

EXAMPLE XIII

Preparation of 3-methyl-2-(1'-isobutenyl)-cyclopropanecarboxylic acid and its dl-allethrolone ester Using the procedure of Example I, (3-methyl-2-butenyl)-p-tolyl sulfone prepared as in French Pat. No. 1,483,715 was reacted with ethyl crotonate to form ethyl 3-methyl-2-(1'-isobutenyl)-cyclopropanecarboxylate having a boiling point of 52° C. at 0.2 mm Hg and a refractive index $n_D^{25}=1.462$ which was hydrolyzed under alkaline conditions to form 3-methyl-2-(1'-isobutenyl)-cyclopropanecarboxylic acid having a boiling point of 81°–82° C. at 0.07 mm Hg and a refractive index $n_D^{25}=1.4820$.

The said acid was reacted with thionyl chloride to form 3-methyl-2-(1'isobutenyl)-cyclopropanecarboxylic acid chloride having a boiling point of 51° C. at 0.8 mm Hg which was then reacted with dl-allethrolone to form 3-methyl-2-(1'-isobutenyl)-cyclopropanecarboxylate of dl-allethrolone having a boiling point of 127° C. at 0.01 mm Hg.

EXAMPLE XIV

Preparation of 3,3-dipropyl-2-(1'-isobutenyl)-cyclopropanecarboxylic acid and its dl-allethrolone ester Using the procedure of Example I, (3-methyl-2-butenyl)-p-tolyl sulfone prepared as in French Pat. No. 1,483,715 was reacted with ethyl β,β-dipropylacrylate to form ethyl 3,3-dipropyl-2-(1'-isobutenyl)-cyclopropanecarboxylate having a boiling point of 90°–92° C. at 0.5 mm Hg and a refractive index $n_D^{17}=1.4660$ which was hydrolyzed under alkaline conditions to form 3,3-dipropyl-2-(1'-isobutenyl)-cyclopropanecarboxylic acid having a boiling point of 116° C. at 0.1 mm Hg and a refractive index $n_D^{23}=1.4760$.

The said acid was reacted with thionyl cholride to form 3,3-dipropyl-2-(1'-isobutenyl)-cyclopropanecarboxylic acid chloride having a boiling point of 80°–85° C. at 0.1 mm Hg and a refractive index $n_D^{23}=1.4819$ which was reacted with dl-allethrolone to form 3,3-dipropyl-2-(1'-isobutenyl)-cyclopropanecarboxylate of dl-allethrolone.

EXAMPLE XV

Preparation of 2-(1'-isobutenyl)-spiro-[2,5]-octane-1-carboxylic acid and its dl-allethrolone ester Using the procedure of Example I, (3-methyl-2-butenyl)-phenyl sulfone prepared as in French Pat. No. 1,483,715 was reacted with ethyl cyclohexylideneacetate to form ethyl 2-(1'-isobutenyl)-spiro-[2,5]-octane-1-carboxylate having a boiling point of 93°–97° C. at 0.7 mm Hg which was hydrolyzed under alkaline conditions to form 2-(1'-isobutenyl)-spiro-[2,5]-octane-1-carboxylic acid having a melting point of 80° C.

The said acid was reacted with thionyl chloride to form 2-(1'-isobutenyl)-spiro[2,5]-octane-1-carboxylic acid chloride having a boiling point of 78°–80° C. at 0.2 mm Hg and a refractive index $n_D^{25}=1.5080$ which was reacted with dl-allethrolone to form 2-(1'-isobutenyl)-spiro-[2,5]-octane-1-carboxylate of dl-allethrolone having a refractive index $n_D^{25}=1.5193$.

EXAMPLE XVI

Preparation of 2-(1'-isobutenyl)-spiro-[2,4]-heptane-1-carboxylic acid and its dl-allethrolone ester Using the procedure of Example XV, (3-methyl-2-butenyl)-phenyl sulfone was reacted with ethyl cyclopentylideneacetate to form ethyl 2-(1'-isobutenyl)-spiro[2,4]-heptane-1-carboxylate which was hydrolyzed under alkaline conditions to form 2-(1'-isobutenyl)-spiro-[2,4]-heptane-1-carboxylic acid.

The said acid was then reacted with thionyl chloride to form 2-(1'-isobutenyl)-spiro-[2,4]-heptane-1-carboxylic acid chloride which was then reacted with dl-allethrolone to form 2-(1'-isobutenyl)-spiro-[2,4]-heptane-1-carboxylate of dl-allethrolone.

EXAMPLE XVII

Preparation of dl-trans 3,3-dimethyl-2-cyclopentylidenemethyl-cyclopropanecarboxylate of cis-cinerolone ester Using the procedure of Example I, 1.15 gm of dl-trans 3,3-dimethyl-2-cyclopentylidenemethylcyclopropanecarboxylic acid chloride produced in Step D of Example IV was reacted with 0.9 gm of cis-cinerolone to form 1.24 gm of dl-trans 3,3-dimethyl-2-cyclopentylidene-methyl-cyclopropanecarboxylate of cis-cinerolone having a refractive index $n_D^{24} = 1.5179$.

EXAMPLE XVIII

Preparation of dl-trans 3,3-dimethyl-2-cyclopentylidene methyl-cyclopropanecarboxylate of 1-oxo-3-methyl-2-(2′ cyclohexenyl)-2-cyclopentene-4-ol Using the procedure of Example I dl-trans 3,3-dimethyl-2-cyclopentylidenemethyl-cyclopropanecarboxylic acid chloride produced as in Step D of Example IV was reacted with 1-oxo-3-methyl-2-(2′-cyclohexenyl)-2-cyclopentene-4-ol (Coll. Czech. Vol. 25, 1960, p. 1835) to form dl-trans 3,3-dimethyl-2-cyclopentylidenemethyl-cyclopropanecarboxylate of 1-oxo-3-methyl-2-(2′-cyclohexenyl)-2-cyclopentene-4-ol having a refractive index of $n_D^{28} = 1.523$.

EXAMLE XIX

Preparation of dl-trans 3,3-dimethyl-2-cyclobutylidenemethyl-cyclopropanecarboxylate of dl-allethrolone Using the procedure of Example I, 1-bromo-2-cyclobutylidene-ethane was reacted with sodium phenyl sulfinate to form (2-cyclobutylidene-ethyl)-phenyl sulfone having a melting point of 76° to 78° C. which was then reacted with ethyl $\beta,\beta$-dimethylacrylate to form ethyl dl-trans 3,3-dimethyl-2-cyclobutylidenemethyl-cyclopropanecarboxylate. The said ethyl ester was hydrolyzed under alkaline conditions to form dl-trans 3,3-dimethyl-2-cyclobutylidenemethyl-cyclopropanecarboxylic acid.

The said acid was reacted with thionyl chloride to form dl-trans 3,3-dimethyl-2-cyclobutylidenemethyl-cyclopropanecarboxylic acid chloride which was then reacted with dl-allethrolone to form dl-trans 3,3-dimethyl-2-cyclobutylidene-methyl-cyclopropanecarboxylate of dl-allethrolone. The compounds obtained at the different steps of the examples VI to XIX are not described in the literature.

EXAMPLE XX

Preparation of dl-cis and trans 2,2,5-trimethyl-spiro-[2,5]-4-octene-1-carboxylic acids and the trans acid ester with dl-allethrolone.

Step A: Preparation of (3-methyl-2-cyclohexenyl)-phenyl sulfone 34.2 gm of raw 3-methyl-2-cyclohexene-1-ol were introduced into 400 cc of formic acid and then 68 gm of sodium phenyl sulfinate were added thereto. The mixture was agitated for 15 hours at room temperature and then was poured into a water-ice mixture. Next, the reaction mixture was extracted with methylene chloride and the methylene chloride extracts were combined, washed first with water, then with an aqueous solution of sodium bicarbonate and again with water, then dried and concentrated to dryness. The residue was admixed with a mixture of isopropyl ether and petroleum ether and the resultant precipitate was isolated by filtration, washed and dried to obtain 47 gm of (3-methyl-2-cyclohexenyl)-phenyl sulfone. A sample of this product was purified by dissolution in methylene chloride, concentration thereof and an addition of isopropyl ether to obtain the said sulfone having a melting point of 70° C.

Analysis: $C_{13}H_{16}O_2S$; molecular weight=236.33. Calculated: C 66.06%; H 6.82%; S 13.57%. Found: 66.3; 6.8; 13.3.

This product is not described in the literature.

Step B: Preparation of ethyl dl-cis and trans 2,2,5-trimethyl-spiro-[2,5]-4-octene-1-carboxylate (a) First, 9.5 gm of potassium tert.-butylate, then 10 gm of (3-methyl-2-cyclohexenyl)-phenyl sulfone were introduced into 50 cc of dimethylsulfoxide containing 1.5% of water, 9.5 cc of ethyl $\beta,\beta$-dimethylacrylate were added over about 5 minutes and the mixture was agitated for 1 hour at room temperature. Then the reaction mixture was cooled to 0° C. and acidified with a dilute aqueous solution of hydrochloric acid. The aqueous phase was extracted with methylene chloride and the methylene chloride extracts were combined. The organic solution obtained was washed first with an aqueous solution of sodium bicarbonate, then with water, dried and concentrated to dryness under pressure to obtain 8.8 gm of substantially pure ethyl dl-trans 2,2,5-trimethyl-spiro-[2,5]-4-octene-1-carboxylate.

This product is not described in the literature.

(b) The same method as described above was repeated but dimethylsulfoxide containing 1.5% of water was replaced with dimethylsulfoxide containing 0.08% of water to obtain substantially pure ethyl dl-cis 2,2,5-trimethyl-spiro-[2,5]-4-octene-1-carboxylate.

This product is not described in the literature.

Step C: (a) Preparation of dl-trans 2,2,5-trimethyl-spiro-[2,5]-4-octene-1-carboxylic acid 1 cc of water and 8.8 gm of ethyl dl-trans 2,2,5-trimethyl-spiro-[2,5]-4-octene-1-carboxylate were introduced into a mixture of 20 cc of methanol and 30 cc of a 2 N methanolic sodium hydroxide solution under an atmosphere of nitrogen. The mixture was brought to reflux and maintained at reflux for 1 hour. Then the methanol was eliminated by distillation and the remainder was diluted with water. The aqueous phase was extracted with ethyl ether and the ether extracts were combined and washed with water. The ether solution, which contained an undesired neutral fraction, was eliminated. All of the aqueous phases were acidified with a dilute aqueous solution of hydrochloric acid and then were extracted with methylene chloride. The methylene chloride extracts were combined, washed with an aqueous solution of sodium chloride, dried and concentrated to dryness. The residue was admixed with isopropyl ether and the precipitate formed was isolated by vacuum filtering and dried to obtain the desired dl-trans 2,2,5-trimethyl-spiro-[2,5]-4-octene-1-carboxylic acid having a double melting point; 122° C., then 130°–132° C.

Analysis: $C_{12}H_{18}O_2$; molecular weight=194.26. Calculated: C 74.19%; H 9.33%. Found: 74.4; 9.3.

The R. M. N. spectra of this product showed an ethylenic proton at 288 Hz which is characteristic of the trans isomer. This product is not described in the literature.

(b) Preparation of dl-cis 2,2,5-trimethyl-spiro-[2,5]-4-octene-1-carboxylic acid By starting with ethyl dl-cis 2,2,5-trimethyl-spiro-[2,5]-4-octene-1-carboxylate and using the same procedure as described for the preparation of trans acid, the dl-cis 2,2,5-trimethyl-spiro-2,5]-4-octene-1-carboxylic acid was obtained having a melting point of 140°–142° C. after recrystallization from isopropyl ether.

Analysis: $C_{12}H_{18}O_2$; molecular weight=194.26. Calculated: C 74.19%; H 9.33%. Found: 74.3; 9.4.

The R. M. N. spectra os this product showed an ethylenic proton at 322 Hz which is characteristic of the cis isomer. This product is not described in the literature.

Step D: Preparation of dl-trans 2,2,5-trimethyl-spiro-[2,5]-4-octene-1-carboxylic acid chloride 2.5 gm of dl-trans 2,2,5-trimethyl-spiro-[2,5]-4-octene-1-carboxylic acid were introduced into a mixture of 15 cc of petroleum ether (boiling point=30°–70° C.) and 5 cc of benzene. Next, 1.4 cc of thionyl chloride were added dropwise and the mixture was agitated for 1 hour at room temperature and then at 60° C. for 20 minutes. Thereafter, 1.4 cc of thionyl chloride were added, and the reaction mixture was agitated for 2 hours and 30 minutes at room temperature. The solvent and the excess thionyl chloride were eliminated by distillation under vacuum.

The residue was rectified under vacuum to obtain 0.836 gm of dl-trans 2,2,5-trimethyl-spiro-[2,5]-4-octene-1-carboxylic acid chloride having a boiling point of 80° C. under 0.5 mm pressure of mercury and it was utilized as such for the next step.

This product is not described in the literature.

Step E: Preparation of dl-trans 2,2,5-trimethyl-spiro-[2,5]-4-octene-1-carboxylate of dl-allethrolone 1 cc of pyridine and 0.836 gm of dl-trans 2,2,5-trimethyl-spiro-[2,5]-4-octene-1-carboxylic acid chloride were introduced into 5 cc of benzene and then a solution of 0.600 gm of dl-allethrolone in 4 cc of benzene was added dropwise. The mixture was agitated for 16 hours at room temperature. Thereafter, the precipitate formed was eliminated by filtration and the benzene filtrate was successively washed with a dilute aqueous solution of hydrochloric acid, with water, with an aqueous solution of sodium bicarbonate and again with water. The solution was dried over magnesium sulfate and concentrated to dryness. The residue was dissolved in cyclohexane and the solution obtained was passed through an alumina column to obtain 0.981 gm of dl-trans 2,2,5-trimethyl-spiro-[2,5]-4-octene-1-carboxylate of dl-allethrolone.

Analysis: $C_{21}H_{28}O_3$; molecular weight=328.43. Calculated: C 76.79%; H 8.59%. Found: 76.7, 8.3.

This product is not described in the literature.

EXAMPLE XXI

Preparation of dl-trans 3,3-dimethyl-2-cyclopropylidenemethyl-1-cyclopropanecarboxylic acid and its dl-allethrolone ester

Step A: Preparation of dl-trans 3,3-dimethyl-2-cyclopropylidenemethyl-1-cyclopropane carboxylic acid 24 gm of cyclopropyl triphenyl phosphonium bromide and 5 gm of a suspension containing 50% of sodium hydride in vaseline oil were introduced into 100 cc of dimethoxyethane. The reaction mixture was heated to reflux and maintained at reflux for 15 minutes after which a mixture of 5.92 gm of dl-trans caronaldehydic acid and 30 cc of dimethoxyethane were added dropwise. The reaction mixture was held at reflux for 1 hour and 30 minutes and then cooled. The insoluble substance formed was eliminated by filtration and the filtrate was concentrated to dryness under reduced pressure. Water was added to the residue and the insoluble matter formed was eliminated by filtration. This filtrate was acidified with a dilute solution of hydrochloric acid and the aqueous acid phase was extracted with ether. The ether extracts were combined, washed with an aqueous saturated solution of sodium chloride, then dried, decolorized with animal charcoal and finally concentrated to dryness under reduced pressure to obtain a partially crystallized product. The crystals were separated from the oily portion by vacuum filtering over fritted glass. The product thus isolated was recrystallized from isopropyl ether to obtain 2.74 gm of dl-trans 3,3-dimethyl-2-cyclopropylidenemethyl-1-cyclopropanecarboxylic acid having a melting point of 85° C.

By starting with the filtrate and the mother liquors of isopropyl ether crystallization and esterification with diazomethane, purification of the product obtained by chromatography and saponification gave a second yield of 0.555 gm of the same acid having a melting point of 84°–85° C. A sample of this product after recrystallization from isopropyl ether had a melting point of 90° C.

Analysis: $C_{10}H_{14}O_2$; molecular weight=166.21. Calculated: C 72.26%; H 8.48%. Found: 72.0; 8.5.

By ozonization of this compound in a chloroform media, followed by decomposition of the ozonide in oxidizing media hydrogen peroxide, the trans caronic acid was obtained (melting point=212° C.), which established the trans structure of the starting cyclopropanecarboxylic acid. This structure was, furthermore, confirmed by the R. M. N. spectra of the compound which had a doublet at 96–101.5 Hz corresponding to the proton in the 1-position of the cyclopropane ring and of which the coupling constant with the proton in the 2-position ($\tau = 5.5$ Hz.) corresponded to a trans structure.

This dl-trans 3,3-dimethyl-2-cyclopropylidenemethyl-1-cyclopropanecarboxylic acid is not described in the literature.

Step B: Preparation of dl-trans 3,3-dimethyl-2-cyclopropylidenemethyl-1-cyclopropanecarboxylic acid chloride 1.1 gm of dl-trans 3,3-dimethyl-2-cyclopropylidenemethyl-1-cyclopropanecarboxylic acid were introduced into 5 cc of benzene and 0.55 cc of thionyl chloride were added over about 15 minutes. Next, the reaction mixture was agitated for 3 hours at room temperature, after which the solvent and the excess thionyl chloride were eliminated by distillation under reduced pressure to obtain 1.2 gm of raw dl-trans 3,3-dimethyl-2-cyclopropylidenemethyl-1-cyclopropanecarboxylic acid chloride. The product was utilized as such for the next step.

This compound is not described in the literature.

Step C: Preparation of dl-trans 3,3-dimethyl-2-cyclopropylidenemethyl-1-cyclopropanecarboxylate of dl-allethrolone First, 1.2 gm of dl-trans 3,3-dimethyl-2-cyclopropylidenemethyl-1-trans cyclopropanecarboxylic acid chloride, then 1.05 gm of dl-allethrolone in solution in 8 cc of benzene were introduced into a mixture of 5 cc of benzene and 1.3 cc of pyridine and the reaction mixture was agitated for 15 hours at room temperature. Then the precipitate formed was eliminated by filtration and the organic filtrate was washed successively, with a dilute aqueous solution of hydrochloric acid, with an aqueous solution of sodium chloride, with an aqueous solution of sodium bicarbonate and lastly again with an aqueous solution of sodium chloride. After having been dried, the solution was concentrated to dryness under reduced pressure. Then the residue was subjected to chromatography through alumina to obtain 1.46 gm of dl-trans 3,3-dimethyl-2-cyclopropylidenemethyl-1-cyclopropanecarboxylate of dl-allethrolone having a refractive index $n_D^{21} = 1.521$.

Analysis: $C_{19}H_{24}O_3$; molecular weight=300.38. Calculated: C 75.97%; H 8.05%. Found: 75.8; 8.1.

Ultraviolet Spectra (in ethanol)

λmax. 223-224 mμ (ε=18,200)

The R. M. N. spectra of this compound showed at 97.5–103 Hz, a doublet which corresponded to the proton in the 1-position of the cyclopropane ring. The coupling constant of this proton and of the proton in the 2-position (τ=5.5 Hz), had, therefore, a value characteristic of the trans structure.

This compound is not described in the literature.

EXAMPLE XXII

Preparation of dl-trans 3,3-dimethyl-2-cyclobutylidene-methyl 1-cyclopropanecarboxylic acid and its dl-allethrolone ester Step A: Preparation of dl-trans 3,3-dimethyl-2-cyclobutylidenemethyl-1-cyclopropanecarboxylic acid.

5.84 gm of a 50% sodium hydride suspension in vaseline oil and 28.5 gm of cyclobutyl triphenyl phosphonium bromide were introduced into 300 cc of dimethoxyethane under an atmosphere of nitrogen. The reaction mixture was brought to reflux and held at reflux for 40 minutes. Then a solution of 6.8 gm of dl-trans caronadelhydic acid in 25 cc of dimethoxyethane was added thereto over about 15 minutes. The reaction mixture was again held at reflux for 30 minutes. The precipitate formed was eliminated by filtration and the filtrate was concentrated to dryness. Water was added to the residue and the precipitate formed was removed by filtration and washed with water. The combined aqueous phases were extracted with ether and the aqueous solution was acidified with a dilute aqueous solution of hydrochloric acid. The aqueous acid solution was extracted with ether and the acid ether extracts were combined, washed with water, dried and concentrated to dryness. The residue was crystallized first from isopropyl ether, then from ether to obtain 4.84 gm of dl-trans 3,3-dimethyl-2-cyclobutylidenemethyl-1-cyclopropanecarboxylic acid having a melting point of 98° C.

Analysis: $C_{11}H_{16}O_2$; molecular weight=180.24 Calculated: C 73.30%; H 8.95%. Found: 73.1; 9.0.

The R. M. N. spectra of this compound showed at 82–87 Hz a doublet which corresponded with the proton in the 1-position of the cyclopropane ring. The coupling constant of this proton and of the proton in the 2-position (τ=5 Hz) had, therefore, a value characteristic of the trans formation.

This compound is not described in the literature.

Step B: Preparation of dl-trans 3,3-dimethyl-2-cyclobutylidenemethyl-1-cyclopropanecarboxylic acid chloride Under an atmosphere of nitrogen, 2 gm of dl-trans 3,3-dimethyl-2-cyclobutylidenemethyl-cyclopropanecarboxylic acid were suspended in 10 cc of petroleum ether, (boiling point=50°-70° C.) and then 1.2 cc of thionyl chloride were added to the reaction mixture which was then agitated for 30 minutes at room temperature. The solvent and the excess thionyl chloride were eliminated by distillation under vacuum and the residue was rectified to obtain 1.88 gm of dl-trans 3,3-dimethyl-2-cyclobutylidene-1-cyclopropanecarboxylic acid chloride having a boiling point of 85° C. at 0.7 mm Hg and a refractive index $n_D^{22} = 1.5090$. The product was utilized as such for the next step.

This compound is not described in the literature.

Step C: Preparation of dl-trans 3,3-dimethyl-2-cyclobutylidenemethyl-1-cyclopropanecarboxylate of dl-allethrolone 1.885 gm of dl-trans 3,3-dimethyl-2-cyclobutylidenemethyl-1-cyclopropanecarboxylic acid chloride were introduced into 5 cc of benzene and then a solution of 1.46 gm of dl-allethrolone in a mixture of 2 cc of pyridine and 10 cc of benzene was added dropwise. Next, the reaction mixture was agitated for 15 hours at room temperature and a few drops of formic acid were added thereto and the reaction mixture was then diluted with water. The organic phase was separated by decanting and the aqueous phase was extracted with ether. The ether extracts were combined with the principal organic phase and the organic solution obtained was washed successively with a dilute aqueous solution of hydrochloric acid, with water with an aqueous solution of sodium bicarbonate and again with water. The solution was dried and concentrated to dryness and the residue was dissolved in benzene. Then the solution was passed through an alumina column and the eluate was concentrated to dryness to obtain 2.74 gm of dl-trans 3,3-dimethyl-2-cyclobutylidenemethyl-1-cyclopropanecarboxylate of dl-allethrolone having a refractive index $n_D^{23} = 1.5192$.

Analysis: $C_{20}H_{26}O_3$; molecular weight=314.41. Calculated: C 76.40%; H 8.34%. Found: 76.1; 8.4.

Ultraviolet Spectra (in ethanol)

γmax. 224-225 mμ (ε=21,200)

This compound is not described in the literature.

EXAMPLE XXIII

Preparation of (5-benzyl-1-furyl-3)-methyl dl-trans 3,3-dimethyl-2-cyclopentylidenemethyl-1-cyclopropanecarboxylate

Step A: Preparation of dl-trans 3,3-dimethyl-2-cyclopentylidenemethyl-1-cyclopropanecarboxylic acid chloride (1) Preparation of the sodium salt of the acid 1.08 gm of dl-trans 3,3-dimethyl-2-cyclopentylidene methyl-1-cyclopropanecarboxylic acid was dissolved in 10 cc of methanol containing 10% water and then sodium methylate was added until alkaline reaction.

Next the methanol was eliminated by distillation under vacuum and benzene was added and the mixture was again distilled in order to completely eliminate the water of the reaction whereby the sodium salt of dl-trans 3,3-dimethyl-2-cyclopentylidenemethyl-1-cyclopropanecarboxylic acid was obtained.

This compound is not described in the literature.

(2) Preparation of the acid chloride

The sodium salt obtained in the preceding step was suspended in 30 cc of benzene and the reaction mixture was cooled after which 2 cc of pyridine, followed by 4.7 cc of oxalyl chloride were added thereto. Next the reaction mixture was agitated and the precipitate formed was eliminated by filtration and washed with benzene. The benzene wash liquors were combined with the principal filtrate to obtain a benzene solution of dl-trans 3,3-dimethyl-2-cyclopentylidenemethyl-1-cyclopropanecarboxylic acid chloride which was used as such for the next step.

Step B: Preparation of (5-benzyl-furyl-3)-methyl dl-trans 3,3-dimethyl-2-cyclopentylidene-methyl-1-cyclopropane carboxylate.

1.5 cc of pyridine and 1.05 gm of (5-benzyl-furyl-3)-methyl alcohol in a solution in 10 cc of benzene were added to the benzene solution of the acid chloride obtained in the preceding. The reaction mixture was agitated for 16 hours at room temperature and then water was added. The organic phase was separated by decanting. The aqueous phase was extracted with ether and the combined organic phases were washed successively with a cold aqueous solution of hydrochloric acid, with water, with an aqueous solution of sodium bicarbonate and again with water, dried and concentrated to dryness. The product thus obtained was dissolved in benzene and the benzene solution was passed through an alumina column and the eluate was concentrated to dryness to obtain 1.234 gm of (5-benzyl-furyl-3)-methyl dl-trans 3,3-dimethyl-2-cyclopentylidenemethyl-1-cyclopropanecarboxylate having a melting point below 40° C. The product was in solid form at room temperature.

Analysis: $C_{24}H_{28}O_3$; molecular weight=364.46. Calculated: C 79.09%; H 7.74%. Found: 79.4; 8.0.

Ultraviolet Spectra (in ethanol)

λmax. at 207–208 mμ (ε=24,000)

This compound is not described in the literature.

EXAMPLE XXIV

Preparation of (5-benzyl-furyl-3)-methyl dl-trans 3,3-dimethyl-2-cyclopentylidenemethyl-1-cyclopropanecarboxylate

Step A: Preparation of d-trans 3,3-dimethyl-2-cyclopentylidenemethyl-1-cyclopropanecarboxylic acid l-ephedrine was reacted with dl-trans 3,3-dimethyl-2-cyclopentylidenemethyl-1-cyclopropanecarboxylic acid in the presence of ethyl acetate. A precipitate was isolated by vacuum filtration which, after purification, led to the l-ephedrine salt of d-trans 3,3-dimethyl-2-cyclopentylidenemethyl-1-cyclopropanecarboxylic acid (salt A) having a melting point of 162° C. and a specific rotation of $[\alpha]_D^{20} = -7°$ (c=1.1% in chloroform).

By acidification of salt A, d-trans 3,3-dimethyl-2-cyclopentylidenemethyl-1-cyclopropanecarboxylic acid having a melting point of 60° C. (slightly pure) and a specific rotation of $[\alpha]_D^{20} = +2°$ (c=1% in chloroform) (acid $A_1$) was obtained.

From the filtrate (ethyl acetate solution) a product was obtained which, after purification, was the l-ephedrine salt of l-trans 3,3-dimethyl-2-cyclopentylidene-methyl-1-cyclopropanecarboxylic acid (salt B) having a melting point of 112° C. and a specific rotation of $[\alpha]_D^{20} = -13°$ (c=1.1% in chloroform).

By acidification of salt B, l-trans 3,3-dimethyl-2-cyclopentylidenemethyl-1-cyclopropanecarboxylic acid having a melting point of 60° C. and a specific rotation of $[\alpha]_D^{20} = 0°$ (c=1% in chloroform) (acid $B_1$) was obtained.

Although the rotatory power of the acids obtained may border on zero, resolution had definitely occurred. In fact, by ozonization of d-trans chrysanthemic acid as well as by ozonization of acid $A_1$ obtained from the ephedrine salt having a melting point of 162° C., the same l-trans caronic acid was arrived at having a melting point of 212° C. and a specific rotation of $[\alpha]_D^{20} = -35°$ (c=1.8% in methanol). [See H. Staudinger and L. Ruzicka, Helv. Chem. Acta 7, 201 (1924)].

The l-ephedrine salt of d-trans 3,3-dimethyl-2-cyclopentylidenemethyl-1-cyclopropanecarboxylic acid, the l-ephedrine salt of l-trans 3,3-dimethyl-2-cyclopentylidenemethyl-1-cyclopropanecarboxylic acid, d-trans 3,3-dimethyl-2-cyclopentylidenemethyl-1-cyclopropanecarboxylic acid and l-trans 3,3-dimethyl-2-cyclopentylidenemethyl-1-cyclopropane carboxylic acid are not described in the literature.

Step B: Preparation of d-trans 3,3-dimethyl-2-cyclopentylidenemethyl-1-cyclopropanecarboxylic acid chloride (1) Preparation of the sodium salt of the said acid.

1.14 gm of d-trans 3,3-dimethyl-2-cyclopentylidenemethyl-1-cyclopropanecarboxylic acid were dissolved in 2 cc of methanol and then sufficient 2.06 N methanolic sodium hydroxide solution was added until alkaline reaction. The methanol was eliminated under reduced pressure and benzene was added to the residue and the solution was again concentrated to dryness under reduced pressure in order to entirely eliminate the water of the reaction whereby the sodium salt of d-trans 3,3-dimethyl-2-cyclopentylidenemethyl-1-cyclopropane carboxylic acid was obtained.

This compound is not described in the literature.

(2) Preparation of the acid chloride

The sodium salt obtained in the preceding step was suspended in 30 cc of benzene and the reaction mixture was cooled. Under an atmosphere of nitrogen, first 2 cc of pyridine, then 4.7 cc of oxalyl chloride were added to the reaction mixture which was then agitated and concentrated to dryness under reduced pressure. Then benzene was added to the residue and the reaction mixture was again concentrated to dryness to entirely eliminate the benzene and oxalyl chloride. The precipitate formed was removed by filtration and was washed with benzene and the benzene wash waters were combined with the principal filtrate to obtain a benzene solution of d-trans 3,3-dimethyl-2-cyclopentylidenemethyl-1-cyclopropanecarboxylic acid chloride which was utilized as such for the next step.

Step C: Preparation of (5-benzyl-furyl-3)-methyl d-trans 3,3-dimethyl-2-cyclopentylidenemethyl-1-cyclopropanecarboxylate.

2 cc of pyridine and 1.12 gm of (5-benzyl-furyl-3) methyl alcohol in solution in 10 cc of benzene were added to the benzene solution of d-trans acid chloride of Step B and the reaction mixture was agitated for 16 hours at room temperature and then diluted with water. The organic phase was separated by decanting and the aqueous phase was extracted with ether and the ether phases were combined with the benzene solution. The organic phase obtained was washed successively with a cold aqueous solution of hydrochloric acid, with water, with an aqueous solution of sodium bicarbonate and again with water, then dried and concentrated to dryness. The residue was dissolved in benzene and the benzene solution obtained was passed through an alumina column and the eluate was concentrated to dryness to obtain 1.3 gm of (5-benzyl-furyl-3)-methyl d-trans 3,3-dimethyl-2-cyclopentylidenemethyl-1-cyclopropanecarboxylate having a refractive index $n_D^{24} = 1.5420$.

Analysis: $C_{24}H_{28}O_3$; Molecular weight = 364.46. Calculated: C 79.09%; H 7.74). Found: 79.1; 7.7.

Ultraviolet Spectra (in ethanol) $\tau$max. at 208 m$\mu$ ($\epsilon = 23,500$) This compound is not described in the literature.

EXAMPLE XXV

Trans-3,3-dimethyl-2-cyclopentylidene-methyl-cyclopropane-1-carboxylic acid (1R,2R)

Step A:
Trans-3,3-dimethyl-2-formyl-cyclopropane-1-carboxylic acid (1R,2R)

30 gm of d-trans chrysanthemic acid (1R,2R) [obtained from d,1-trans cis-chrysanthemic acid by crystallization of its D(−)-threo-1-p-nitrophenyl-2-dimethylaminopropane-1,3-diol salt as described in copending, commonly assigned U.S. patent application Ser. No. 742,532 filed July 5, 1968, and entitled: "Novel resolution process"] were dissolved in 375 cc of methanol and after cooling the solution to −80° C., an ozonized oxygen current was bubbled through the solution until a blue color appeared. Then an oxygen current was bubbled through the solution for 15 minutes followed by a nitrogen current for 45 minutes. 15 cc of dimethyl sulfide were slowly added to the solution and the reaction mixture was held for 30 minutes at −35° C., then for 1 hour at 0° C. and finally 1 hour at room temperature. The methanol was removed by distillation under reduced pressure and the residue was added to a solution of 25.5 gm of trimethylamino-acetohydrazide chloride (reagent T) in 250 cc of ethanol and 25 cc of acetic acid. The reaction mixture was heated to reflux and held there for one hour and then cooled. The mixture was poured into a dilute solution of sodium hydroxide and then was extracted with ether to remove any non-aldehyde fraction. The mixture was then made acidic with dilute aqueous hydrochloric acid and the aqueous phase was extracted with ether. The ether extracts were washed, dried and concentrated to dryness. The residue was pasted with petroleum ether (boiling point = 35°–75° C.) to obtain 8.7 gm of trans-3,3-dimethyl-2-formyl-cyclopropane-1-carboxylic acid (1R,2R).

Step B:
Trans-3,3-dimethyl-2-cyclopentylidene-methyl-cyclopropane-1-carboxylic acid (1R,2R)

24.66 gm of triphenyl-cyclopentylphosphonium bromide (prepared by method of Ramirez et al, J.A.C.S., vol. 79, 1957, p. 67) was added under a nitrogen atmosphere to 100 cc of dimethoxyethane and then 97 cc of a 1.3 N solution of butyl lithium in hexane was progressively added to the reaction mixture. The mixture was stirred for 2 hours at room temperature and then a solution of 5.7 gm of trans-3,3-dimethyl-2-formyl-cyclopropane-1-carboxylic acid (1R,2R) in 30 cc of dimethoxyethane was added thereto with stirring at a temperature less than 60° C. The mixture was stirred for 2 hours at 60° C., cooled and then concentrated to dryness by distillation under reduced pressure. The residue was added to water with stirring and the aqueous mixture was extracted with ether. The ether extracts were discarded and the aqueous phase was adjusted to a pH of 4.7 with dilute hydrochloric acid. The aqueous acid phase was extracted with ether and the ether extract was washed with water, dried and concentrated to dryness under reduced pressure. The oily residue was added to 10 gm of reagent T in 100 cc of ethanol and 20 cc of acetic acid. The reaction mixture was heated to reflux and held there for 1 hour. After cooling, the mixture was made alkaline with aqueous sodium hydroxide and was extracted with ether. The combined ether extracts were dried and evaporated to dryness to obtain 3.85 gm of crude acid.

The crude acid was dissolved in 11 cc of ethyl acetate and a solution of 3.2 gm of 1-ephedrine in 11 cc of ethyl acetate was added thereto. After standing, the mixture was vacuum filtered to obtain 5.55 gm of 1-ephedrine salt of trans-3,3-dimethyl-2-cyclopentylidene-methyl-cyclopropane-1-carboxylic acid (1R,2R) melting at 158° C. and after recrystallization from ethyl acetate melting at 160° C. and having a specific rotation $[\alpha]_D = -6°$ (c = 0.25% in chloroform).

The said product was then made acidic by addition to aqueous dilute hydrochloric acid and the acid aqueous phase was extracted with ether. The ether phase was washed with water, dried and distilled to dryness under reduced pressure. A small amount of petroleum ether was added to the residue to cause crystallization of 2.70 gm of trans-3,3-dimethyl-2-cyclopentylidene-methyl-cyclopropane-1-carboxylic acid (1R,2R) melting at about 35° C. and having a specific rotation $[\alpha]_D^{20} = +5°$ (c=0.35% in chloroform). N.M.R.. Spectrum (deuterochloroform):

The N.M.R. spectrum has the following characteristics:
- peaks at 71 and 79 hz, corresponding to the methyl hydrogens at 3,
- peaks at 82.5 and 87.5 hz, corresponding to the hydrogen at position 1 (doublet)
- peaks at 100 and 135 hz, corresponding to the hydrogens of the cyclopentane cycle,
- peak at 695 hz, corresponding to the carboxyl hydrogen.

EXAMPLE XXVI l-trans chrysanthemic acid (1S,2S) was obtained from dl-trans-cis chrysanthemic acid by precipitation of its L(+)-threo-1-p-nitrophenyl-2-dimethylaminopropane-1,3-diol salt thereof as described in copending, commonly assigned U.S. patent application Ser. No. 742,532 filed July 5, 1968 and entitled NOVEL RESOLUTION PROCESS. Using the procedure of Step A of Example XXV, 1-trans chrysanthemic acid (1S,2S) was reacted to obtain trans-3,3-dimethyl-2-formylcyclopropane-1-carboxylic acid (1S,2S).

Using the procedure of Step B of Example XXV, trans-3,3-dimethyl-2-formyl-cyclopropane-1-carboxylic acid (1S,2S) was reacted to form trans-3,3-dimethyl-2-cyclopentylidene-methylcyclopropane-1-carboxylic acid (1S,2S) having a specific rotation $[\alpha]_D^{20} = 0°$ (c=1% in chloroform). The product was identical to that described above under the name of l-trans-3,3-dimethyl-2-cyclopentylidene-methyl-cyclopropane-1-carboxylic acid or acid B₁.

EXAMPLE XXVII

Trans 3,3-dimethyl-2-cyclopentylidenemethyl-cyclopropane-1-carboxylic acid (1R,2R)

86.5 gm of triphenylcyclopentyl-phosphonium bromide was added under a nitrogen atmosphere to 350 cc of dimethoxyethane and then 340 cc of a 1.3 N solution of butyl lithium in hexane was added thereto. The reaction mixture was stirred for 2 hours at room temperature and then a solution of 20 gm of trans-3,3-dimethyl-2-formyl-cyclopropane-1-carboxylic acid (1R,2R) in 105 cc of dimethoxyethane was added thereto at a temperature not above 60° C. The reaction mixture was stirred at 60° C. for 2 hours and then cooled and evaporated to dryness under reduced pressure. The residue was added to water with stirring and the aqueous mixture was extracted with ether. The ether extracts were discarded and the aqueous phase was made adjusted to a pH of 4.7 with dilute hydrochloric acid. The acid aqueous phase was extracted with ether and the combined ether extracts were washed with water, dried and evaporated to dryness under reduced pressure. The oily residue was admixed with 80 cc of ethyl acetate. The mixture was vacuum filtered and the precipitate was washed with ethyl acetate to obtain 21 gm of crude acid.

The crude acid was added to a solution of 22.5 gm of l-ephedrine in 90 cc of ethyl acetate and the mixture was allowed to stand to effect crystallization. The mixture was vacuum filtered and the precipitate was washed with ethyl acetate and dried to obtain 27 gm of l-ephedrine salt of trans-3,3-dimethyl-2-cyclopentylidene-methyl-cyclopropane-1-carboxylic acid (1R,2R) melting at 160° C. and having a specific rotation $[\alpha]_D^{20} = -5.5°$ (c=0.35% in chloroform). The said salt was acidified as in Example XXV to obtain almost a quantitative yield of trans-3,3-dimethyl-2-cyclopentylidene-methylcyclopropane-1-carboxylic acid (1R,2R), with respect to the ephedrine salt.

EXAMPLE XXVIII

Trans-3,3-dimethyl-2-cyclopentylidene-methyl-cyclopropane-1-carboxylic acid (1R,2R)

Step A: Methyl trans-3,3-dimethyl-2-cyclopentylidene-methyl-cyclopropane-1-carboxylate (1R,2R)

53 gm of triphenylcyclopentylphosphonium bromide were added under inert atmosphere to 160 cc of dimethyl sulfoxide to which was then added 11.6 gm of sodium methylate. After stirring the reaction mixture for one hour at room temperature, 13.4 gm of the methyl ester of trans-3,3-dimethyl-2-formylcyclopropane-1-carboxylic acid (1R,2R) [obtained as described in copending U.S. patent application Ser. No. 841,140 filed July 11, 1969] were added to the reaction mixture over 30 minutes and the mixture was then stirred for 21 hours at room temperature. The reaction was poured into an ice-aqueous hydrochloric acid and cyclohexane was added thereto. The mixture was stirred, filtered to eliminate triphenylphosphine and the organic phase was decanted off. The aqueous phase was extracted with cyclohexane and the organic phases were combined, washed successively with water, with aqueous sodium bicarbonate and then with water, dried and evaporated to dryness under reduced pressure. The residue was redistilled to obtain 17.29 gm of methyl trans-3,3-dimethyl-2-cyclopentylidene-methyl-cyclopropane-1-carboxylate (1R,2R) boiling at 82° C. at 0.5 mm Hg and having a specific rotation $[\alpha]_D = +5°$ (c=1% in chloroform). The saponification index was 271 gm (269 theoretical) of potassium hydroxide per gm.

The N.M.R. spectrum (in deutero chloroform) has the following characteristics:
- peaks at 43–44 hz corresponding to hydrogen at positon 1,
- peaks at 70–77 hz corresponding to the methyl hydrogens at position 3,
- peaks at 95–105 and 130–140 hz corresponding to the hydrogens of the cyclopentane cycle,
- peaks at 227 hz corresponding to methyl hydrogen of the methoxy carbonyl radical,
- peaks at 255.5–305.5 hz corresponding to the methyl hydrogen of the cyclopentylidene methyl radical.

Step B: trans-3,3-dimethyl-2-cyclopentylidene-methyl-cyclopropane-1-carboxylic acid (1R,2R)

10 gm of the product of step A was added under inert atmosphere to a mixture of 10 cc of methanol and 10 cc of water and 5 cc of an aqueous solution of 10 N potassium hydroxide was added thereto. The reaction mixture was heated at reflux for 1½ hours and the methanol was distilled off at atmospheric pressure. Water and isopropyl ether were added to the reaction mixture which was then made acidic with aqueous hydrochloric acid. The organic phase was decanted off and the aqueous phase was extracted with isopropyl ether. The combined organic phases were washed with water and then evaporated to dryness under reduced pressure to obtain 9.25 gm of trans-3,3-dimethyl-2-cyclopentylidene-methyl-cyclopropane-1-carboxylic acid (1R,2R) having a specific rotation $[\alpha]_D = +5°$ (c=0.35% in chloroform).

N.M.R. Spectrum (deuterochloroform)

The N.M.R. spectrum has the following characteristics:
- peaks at 71 and 79 hz corresponding to the methyl hydrogens at 3,
- peaks at 82.5 and 87.5 hz corresponding to the hydrogen in position 1 (doublet)
- peaks at 100 and 135 hz, corresponding to the hydrogens of the cyclopentane cycle,
- peaks at 695 hz corresponding to the carboxyl hydrogen.

In an analogous way, starting from the methyl esters of trans-3,3-dimethyl-2-formyl-cyclopropane-1-carboxylic (1S,2S) or racemic acids, trans-3,3-dimethyl-2-cyclopentylidene-methyl-cyclopropane-1-carboxylic (1S,2S) or racemic acids were obtained.

EXAMPLE XXIX

Trans-3,3-dimethyl-2-(2'-ethyl-1'-butenyl)-cyclopropane-1-carboxylic acid (1R,2R)

Step A: Methyl ester of trans-3,3-dimethyl-2-(2'-ethyl-1'-butenyl)-cyclopropane-1-carboxylic acid (1R,2R)

23 gm of triphenyl-3-pentyl-phosphonium iodide were added under an inert atmosphere to 200 cc of benzene and 29.8 cc of 1.68 N hexane solution of butyl lithium was added thereto. The mixture was stirred for 2 hours at room temperature and then a solution of 9.15 gm of methyl trans-3,3-dimethyl-2-formyl-cyclopropane-1-carboxylate (1R,2R) in 20 cc of benzene was slowly added thereto and then stirred for 2 hours at room temperature. After the addition of water, the reaction mixture was filtered to remove insolubles and the organic phase was decanted off. The aqueous phase was extracted with ether and the organic phases were combined, dried and concentrated to dryness under reduced pressure. The residue was added to petroleum ether b.p.=67°-75° C. and the mixture was filtered to remove triphenyl phosphine oxide. The filtrate was evaporated to dryness under reduced pressure to obtain 9.67 gm of methyl trans-3,3-dimethyl-2-(2'-ethyl-1'-butenyl)-cyclopropane-1-carboxylate (1R,2R).

Step B: Trans-3,3-dimethyl-2-(2'-ethyl-1'-butenyl)-cyclopropane-1-carboxylic acid (1R,2R)

9.67 gm of the product of Step A was added under an inert atmosphere to a mixture of 35 cc of 2 N aqueous sodium hydroxide and 70 cc of methanol and the reaction mixture was heated to reflux and was held there for 2 hours. The methanol was distilled off and water was added thereto. The aqueous phase was extracted with ether and the ether phase was removed. The aqueous phase was made acidic with aqueous hydrochloric acid. The ether phases were combined, dried and evaporated to dryness. The residue was redistilled under reduced pressure and the middle fraction of 5.87 gm and having a boiling point of 96° C. at 0.15 mm Hg was dissolved in 50cc of ethanol and 5 cc of acetic acid. 5 gm of Reagent T was added to the reaction mixture which was then heated to reflux and held there for 1½ hours. After cooling the reaction mixture was poured into dilute aqueous sodium hydroxide and the mixture was extracted with ether. The ether phases were dried and evaporated to dryness to obtain 5.03 gm of trans-3,3-dimethyl-2-(2'-ethyl-1'-butenyl)-cyclopropane-1-carboxylic acid (1R,2R) having a specific rotation $[\alpha]_D = 28.5°$ (c=1.4% in ethanol).

U. V. spectrum (ethanol)

max. at 200-201 nm ($E_1{}_{cm}{}^{1}\% = 611$)

N.M.R. Spectrum (deuterochloroform)

The N.M.R. spectrum showed the following characteristic:
- peaks at 51.5-59-66 hz corresponding to the methyl hydrogens of the 2'-ethyl-butenyl radical,
- peaks at 69-78.5 hz corresponding to the methyl hydrogens at position 3,
- peaks at 81-86 hz corresponding to the hydrogen at position 1,
- peaks at 124 hz corresponding to the $CH_2$ of the 2'-ethyl-butenyl radical,
- peaks at 287-295 hz corresponding to the ethylene hydrogen of the butenyl radical,
- peaks at 676 hz corresponding to the carboxyl hydrogen.

Various modifications of the process of the invention may be made without departing from the spirit or scope thereof and it is to be understood that the invention is to be limited only as defined in the appended claims.

We claim:

1. A compound selected from the group consisting of racemic or optically-active cyclopropane carboxylic derivative having the formula

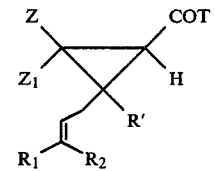

wherein Z and $Z_1$ are selected from the group consisting of lower alkyl having from 1 to 7 carbon atoms and phenyl and Z and $Z_1$ together represent an alkylene residue having 4 to 5 carbon atoms, T is chlorine, $R_1$ and $R_2$ together represent an alkylene residue having 3 to 7 carbon atoms, R' is selected from the group consisting of hydrogen and lower alkyl.

2. A compound of claim 1 wherein R' is hydrogen in trans configuration in relation to the carboxylic chain and $R_1$ and $R_2$ together for an alkylidene of 2 to 5 carbon atoms.

3. A compound of claim 2 wherein $R_1$ and $R_2$ together form a butylidene chain.

* * * * *